United States Patent
Aoki

(10) Patent No.: US 10,870,643 B2
(45) Date of Patent: Dec. 22, 2020

(54) METHOD FOR MANUFACTURING 1,3-DIOXANE-5-ONE

(71) Applicant: KAO CORPORATION, Tokyo (JP)

(72) Inventor: Takashi Aoki, Wakayama (JP)

(73) Assignee: KAO CORPORATION, Tokyo (JP)

( * ) Notice: Subject to any disclaimer, the term of this patent is extended or adjusted under 35 U.S.C. 154(b) by 0 days.

(21) Appl. No.: 16/473,065

(22) PCT Filed: Dec. 26, 2017

(86) PCT No.: PCT/JP2017/046813
§ 371 (c)(1),
(2) Date: Jun. 24, 2019

(87) PCT Pub. No.: WO2018/124147
PCT Pub. Date: Jul. 5, 2018

(65) Prior Publication Data
US 2019/0330173 A1   Oct. 31, 2019

(30) Foreign Application Priority Data

Dec. 27, 2016 (JP) ................................. 2016-253829
Dec. 27, 2016 (JP) ................................. 2016-253833
Dec. 27, 2016 (JP) ................................. 2016-253836
Dec. 27, 2016 (JP) ................................. 2016-253843

(51) Int. Cl.
C07B 61/00 (2006.01)
C07C 45/65 (2006.01)
C07C 213/00 (2006.01)
C07D 319/06 (2006.01)
C07C 49/17 (2006.01)
C07C 215/10 (2006.01)
C07D 407/12 (2006.01)
C07D 317/32 (2006.01)
C07B 41/12 (2006.01)

(52) U.S. Cl.
CPC ............ C07D 407/12 (2013.01); C07B 61/00 (2013.01); C07C 45/65 (2013.01); C07C 213/00 (2013.01); C07D 317/32 (2013.01); C07D 319/06 (2013.01); C07B 41/12 (2013.01); C07C 49/17 (2013.01); C07C 215/10 (2013.01)

(58) Field of Classification Search
None
See application file for complete search history.

(56) References Cited

U.S. PATENT DOCUMENTS

| 5,821,374 | A | 10/1998 | Jenny et al. |
| 7,851,639 | B2 | 12/2010 | Hayat et al. |
| 2007/0197790 | A1 | 8/2007 | Belgsir et al. |
| 2012/0014889 | A1 | 1/2012 | Miller et al. |

FOREIGN PATENT DOCUMENTS

| CN | 1939904 A | 4/2007 |
| CN | 101412706 A | 4/2009 |
| DE | 3900479 A1 | 7/1990 |
| EP | 1669353 A1 | 6/2006 |
| JP | 2006-219406 A | 8/2006 |
| WO | WO 2012/041845 A1 | 4/2012 |
| WO | WO 2014/140017 A1 | 9/2014 |

(Continued)

OTHER PUBLICATIONS

Animati et al, Bioorganic & Medicinal Chemistry Letters, vol. 22, pp. 5013-5017 (Year: 2012).*
U.S. Office Action for U.S. Appl. No. 16/473,177, dated Sep. 5, 2019.
Waidmann et al., "Using combinations of oxidants and bases as PCET reactants: thermochemical and practical considerations," Energy Environ. Sci., vol. 5, Feb. 21, 2012, pp. 7771-7780.
Bobbitt et al., "Oxoammonium Salt Oxidations of Alcohols in the Presence of Pyridine Bases," J. Org. Chem., vol. 79, No. 3, 2014 (Date of Publication Jan. 6, 2014), pp. S1-S56 (57 total pages).
Cao et al., "Aerobic Oxidation Catalysis with Stable Radicals," Chem. Commun, vol. 50, 2014 (Published on Mar. 12, 2014), pp. 4524-4543.
Indian Office Action, dated Oct. 1, 2019, for Indian Application No. 201917000304, with an English translation.

(Continued)

Primary Examiner — Zinna Northington Davis
(74) Attorney, Agent, or Firm — Birch, Stewart, Kolasch & Birch, LLP

(57) ABSTRACT

The present invention relates to a method for producing a 1,3-dioxan-5-one by a short-step and simple method from raw materials that are procurable easily and inexpensively, using, as a raw material, a 1,3-dioxane that is a mixture containing a 1,3-dioxolane. Provided is a method for producing a 1,3-dioxan-5-one, including using a mixture of a compound represented by the following formula (I) and a compound represented by the following formula (II) as a raw material, the method including a step of oxidizing the mixture under an oxidative esterification condition (step 2):

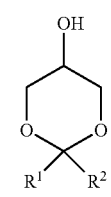

(I)

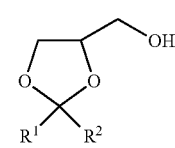

(II)

wherein, in the formulae (I) and (II), $R^1$ and $R^2$ each independently represent a hydrogen atom or a monovalent hydrocarbon group, or $R^1$ and $R^2$ are bonded to each other to form a divalent hydrocarbon group for constituting a ring structure.

14 Claims, 4 Drawing Sheets

(56) References Cited

FOREIGN PATENT DOCUMENTS

| WO | WO 2015/181747 A1 | 12/2015 |
|---|---|---|
| WO | WO 2016/097840 A1 | 6/2016 |

OTHER PUBLICATIONS

Indian Office Action, dated Oct. 11, 2019, for Indian Application No. 201917000294, with an English translation.
Indian Office Action, dated Oct. 4, 2019, for Indian Application No. 201917000301, with an English translation.
Okada et al., "Sodium Hypochlorite Pentahydrate (NaOCl•5H$_2$0) Crystals as an Extraordinary Oxidant for Primary and Secondary Alcohols," Synlett, vol. 25, No. 4, 2014, pp. 596-598 (5 total pages).
Abramovich et al., "Organocatalytic Oxidative Dimerization of Alcohols to Esters", Synlett, vol. 23, No. 15, pp. 2261-2265. (2012).
Badalyan et al., "Cooperative Electrocatalytic Alcohol Oxidation with Electron-Proton-Transfer Mediators", Nature, vol. 535, No. 7612, 2016, pp. 406-410.
De Luca et al., "Trichloroisocyanuric/TEMPO Oxidation of Alcohols under Mild Conditions: A Close Investigation", Journal of Organic Chemistry, vol. 68, No. 12, 2003, pp. 4999-5001.
English translation of Decision to Grant a Patent for Japanese Patent Application No. 2017-250263, dated Aug. 24, 2018.
English translation of Decision to Grant a Patent for Japanese Patent Application No. 2017-250264, dated Aug. 15, 2018.
English translation of Decision to Grant a Patent for Japanese Patent Application No. 2017-250267, dated Aug. 24, 2018.
English translation of Descision to Grant a Patent for Japanese Application No. 2017-250262, dated Aug. 28, 2018.
English translation of Notice of Reasons for Refusal for Japanese Patent Application No. 2017-250262, dated Jun. 18, 2018.
English translation of Notice of Reasons for Refusal for Japanese Patent Application No. 2017-250263, dated Jun. 4, 2018.
English translation of Notice of Reasons for Refusal for Japanese Patent Application No. 2017-250264, dated Jun. 4, 2018.
English translation of Notice of Reasons for Refusal for Japanese Patent Application No. 2017-250267, dated Jun. 4, 2018.
Ermolenko et al., "An Expedient One-Step Preparation of (S)-2,3-O-Isopropylidene-glyceraldehyde", Synlett, vol. 10, 2001, pp. 1565-1566.
Hamlin et al., "Dehydrogenation of Perfluoroalkyl Ketones by Using a Recyclable Oxoammonium Salt", European Journal of Organic Chemistry, vol. 18, 2013, pp. 3658-3661.
Herath et al., 2,2,6,6-Tetramethyl piperidine-1-oxyl (TEMPO)-mediated catalytic oxidation of benzyl alcohol in acetonitrile and ionic liquid 1-butyl-3-methyl-imidazolium hexafluorophosphate [BMim][PF$_6$]: Kinetic analysis, Electrochimica Acta, vol. 53, No. 12, 2008, pp. 4324-4330.
Hon et al., "Tishchenko Reactions and Oppenauer Oxidation Reactions of Aldehydes Promoted by Diisobutylaluminum Hydride", Tetrahedron Letters, vol. 45, No. 16, 2004, pp. 3313-3315.
Hon et al., "Tishchenko Reactions of Aldehydes Promoted by Diisobutylaluminum Hydride and its Application of the Macrocyclic Lactone Formation", Tetrahedron, vol. 63, No. 46, 2007, pp. 11325-11340.
International Search Report for International Application No. PCT/JP2017/046813 dated Mar. 20, 2018.
Kataky et al., "Chiral Resolution of R and S 1-Phenylethanol on Glassy Carbon Electrodes", Journal of Electroanalytical Chemistry, vol. 633, No. 1, 2009, pp. 57-62.
Li et al., "α-Aminoxylation of Ketones and β-Chloro-α-aminoxylation of Enones with TEMPO and Chlorocatecholborane", Organic Letters, vol. 14, No. 17, 2012, pp. 4474-4477.
Merbouh et al., "Oxoammonium Salts. 9. Oxidative Dimerization of Polyfunctional Primary Alcohols to Esters. An Interesting β Oxygen Effect", Journal of Organic Chemistry, vol. 69, No. 15, 2004, pp. 5116-5119.
Shibuya et al., "2-Azaadamantane N-Oxyl (AZADO and I-Me-AZADO: High Efficient Organocatalysts for Oxidation of Alcohols", Journal of the American Chemical Society, vol. 128, No. 26, 2006, pp. 8412-8413.
Sorbye et al., Preparation of Protected Serinol, Synthetic Communications, vol. 27, No. 16, 1997, pp. 2813-2816.
Wang et al., "Domino Radical Addition/Oxidation Sequence with Photocatalysis: One-Pot Synthesis of Polysubstituted Furans from α-Chloro-Alkyl Ketones and Styrenes", Chemistry A European Journal, vol. 22, No. 39, Aug. 19, 2016, pp. 13794-13798.
Wang et al., "The indirect conversion of glycerol into 1,3-dihydroxyacetone over magnetic polystyrene immobilized TEMPO catalyst", Chemical Engineering Journal, vol. 229, 2013, pp. 234-238.
Zheng et al. "Novel Process for 1,3-Dihydroxyacetone Production from Glycerol. 1. Technological Feasibility Study and Process Design" Industrial & Engineering Chemistry Research, vol. 51, 2012, pp. 3715-3721.
U.S. Appl. No. 16/473,167, filed Jun. 24, 2019, Not yet assigned.
U.S. Appl. No. 16/473,177, filed Jun. 24, 2019, Not yet assigned.
Carlsen et al., "Synthesis of benzylidene-protected dihydroxyacetone," Acta Chemica Scandinavica, vol. 50, 1996, pp. 185-187.
Extended European Search Report for European Application No. 17888167.8, dated Jul. 14, 2020.
Majewski et al., "1, 3-Dioxan-5-ones: synthesis, deprotonation, and reactions of their lithium enolates," Canadian Journal of Chemistry, vol. 73, 1995, pp. 1616-1626.
Trost et al., "Palladium-catalyzed trimethylenemethane reaction to form methylenetetrahydrofurans. Aldehyde and ketone substrates and the tin effect," Journal of the American Chemical Society, vol. 111, No. 15, 1989, pp. 5902-5915.
International Search Report for International Application No. PCT/JP2017/046814 dated Feb. 6, 2018.
International Search Report for International Application No. PCT/JP2017/046815 dated Feb. 6, 2018.
Extended European Search Report dated Aug. 17, 2020 for Application No. 17885459.2.
Sproge et al., "Selective liquid phase oxidation of glycerol to glyceric acid over novel supported Pt catalysts", J. Serb. Chem. Soc., vol. 78, No. 9, 2013, pp. 1359-1372.

* cited by examiner

[Fig. 1]
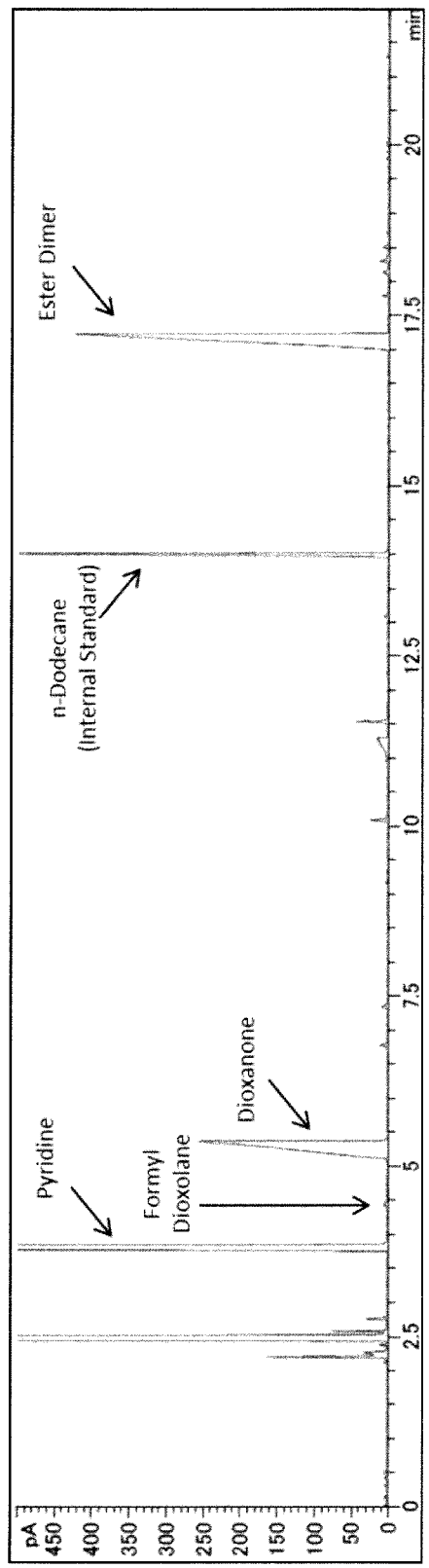

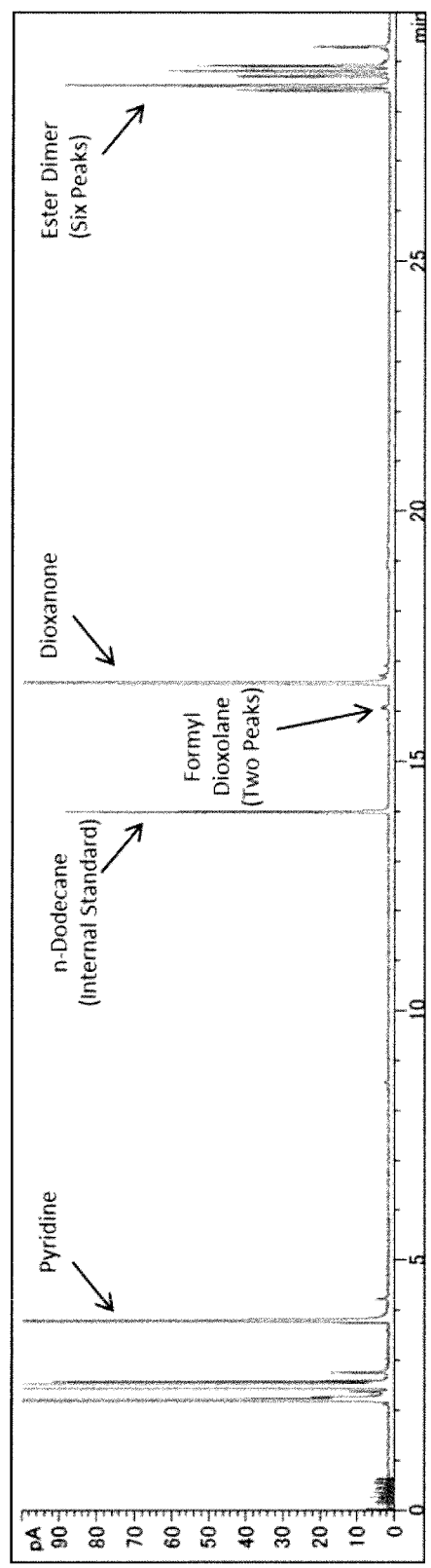
[Fig. 2]

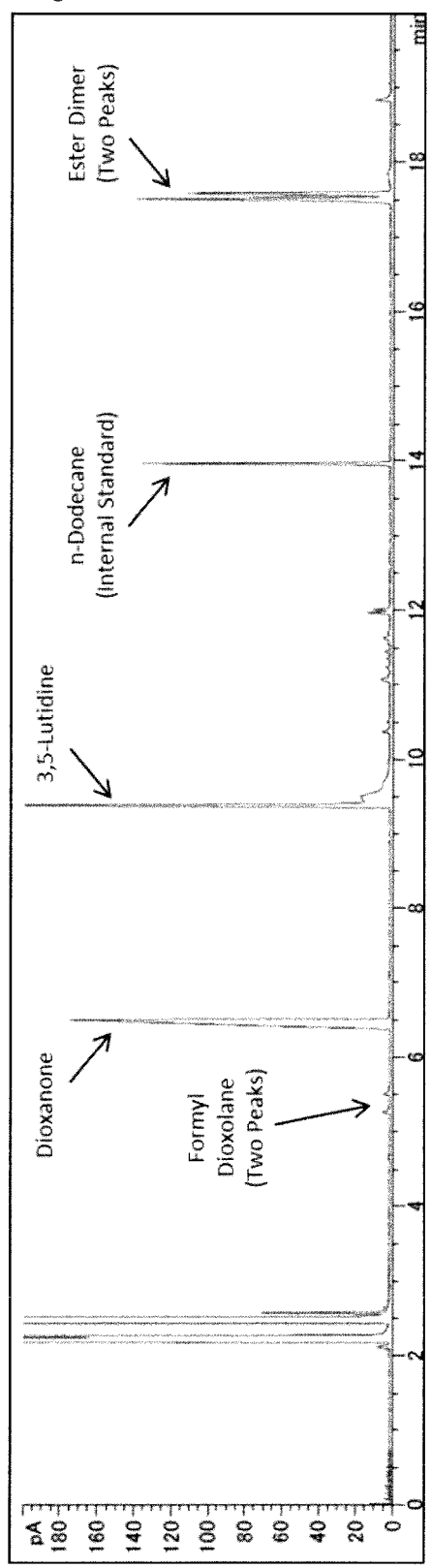
[Fig. 3]

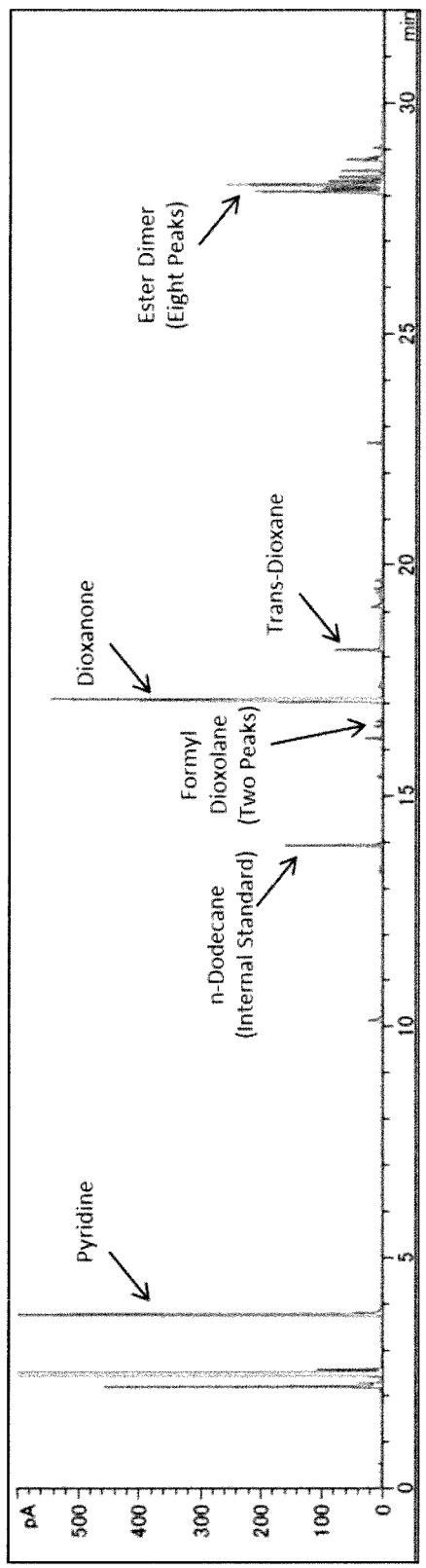
[Fig. 4]

METHOD FOR MANUFACTURING 1,3-DIOXANE-5-ONE

FIELD OF THE INVENTION

The present invention relates to a method for producing a 1,3-dioxan-5-one.

BACKGROUND OF THE INVENTION

A 1,3-dioxan-5-one is useful as a synthetic intermediate for various useful compounds.

For example, Industrial & Engineering Chemistry Research, Vol. 51, pp. 3715-3721, 2012 (NPL 1) discloses a method of producing dihydroxyacetone (hereinafter also referred to as "DHA") through a deprotection reaction (deacetalization reaction) of 2-phenyl-1,3-dioxan-5-one.

In addition, Synthetic Communications, Vol. 27, No. 16, pp. 2813-2816, 1997 (NPL 2) discloses a method of producing an acetal form of 2-amino-1,3-propanediol (hereinafter also referred to as "serinol") that is useful as a raw material for an X-ray contrast agent from 2-phenyl-1,3-dioxan-5-one, and U.S. Pat. No. 7,851,639 (PTL 1) discloses various examples of carbon skeleton construction through an asymmetric aldol reaction between a 1,3-dioxan-5-one and an aldehyde.

As a method of producing a 1,3-dioxan-5-one, for example, Journal of the American Chemical Society, Vol. 111, pp. 5902-5915, 1989 (NPL 3) discloses a production method using, as a raw material, trishydroxymethyl nitromethane or trishydroxymethyl aminomethane, which is inducible from nitromethane that is procurable on an industrial scale.

NPL 1 discloses a method of producing 2-phenyl-1,3-dioxan-5-one by oxidizing high-purity 2-phenyl-1,3-dioxan-5-ol that is obtained through low-temperature recrystallization of an isomer mixture of four kinds composed of cis- and trans-2-phenyl-1,3-dioxan-5-ol and cis- and trans-4-hydroxymethyl-2-phenyl-1,3-dioxolane.

In addition, DE 3900479 A (PTL 2) discloses a method of producing a 1,3-dioxan-5-one by subjecting a mixture of a 1,3-dioxan-5-one and 1,3-dioxolane-4-carboaldehyde (4-formyl-1,3-dioxolane), that is obtained by oxidizing glycerol formal producible from inexpensively procurable glycerol (glycerin) and formaldehyde, to separation through precision distillation.

SUMMARY OF THE INVENTION

The present invention relates to a method for producing a 1,3-dioxan-5-one, including using a mixture of a compound represented by the following formula (I) and a compound represented by the following formula (II) as a raw material, the method including a step of oxidizing the mixture under an oxidative esterification condition (step 2). Here, the step 2 is a step of oxidizing the compound represented by the formula (I) under the condition under which in the mixture, the compound represented by the formula (II) is oxidatively esterified.

Furthermore, the present invention relates to a method for producing 1,3-dihydroxyacetone through deacetalization of the resulting 1,3-dioxan-5-one. In addition, the present invention relates to a method for producing 2-amino-1,3-propanediol through reductive amination of the resulting 1,3-dioxan-5-one, followed by deacetalization:

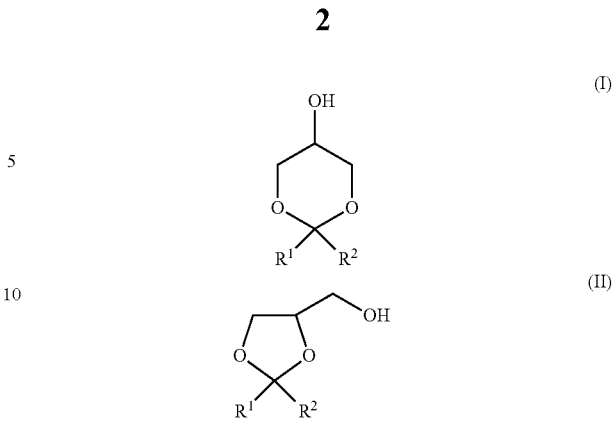

wherein, in the formulae (I) and (II), $R^1$ and $R^2$ each independently represent a hydrogen atom or a monovalent hydrocarbon group, or $R^1$ and $R^2$ are bonded to each other to form a divalent hydrocarbon group for constituting a ring structure.

BRIEF DESCRIPTION OF THE DRAWINGS

FIG. 1 is a GC chart of a reaction solution obtained in Example 1-1.

FIG. 2 is a GC chart of a reaction solution obtained in Example 2-1.

FIG. 3 is a GC chart of a reaction solution obtained in Example 3-3.

FIG. 4 is a GC chart of a reaction solution obtained in Example 4.

DETAILED DESCRIPTION OF THE INVENTION

Though a 1,3-dioxan-5-one is useful as a synthetic intermediate for various useful compounds, any technology for inexpensively producing a high-quality 1,3-dioxan-5-one from easily available raw materials through an industrially advantageous method has not been established yet.

For example, the production method of NPL 3 is a multi-stage synthesis method from starting raw materials which are highly risky in explosion and expensive, and furthermore, it is required to use an expensive oxidizing agent in a stoichiometric amount or more in an oxidative cleavage process, and hence, the production method of NPL 3 is not suitable for production on an industrial scale.

In the production method of NPL 1, the yield of 2-phenyl-1,3-dioxan-5-ol after recrystallization is very low as 25%, and a measure of reducing the loss amount of raw materials by reusing the recrystallization mother liquid for the subsequent acetalization reaction is presented. However, a problem that the productivity of from the reaction to the purification is remarkably low is not solved, and thus, it is hardly said that the production method of NPL 1 is suitable for production on an industrial scale.

In addition, in the production method of PTL 2, in order to separate the 1,3-dioxan-5-one from the oxidation mixture containing, as main components, the 1,3-dioxan-5-one and 4-formyl-1,3-dioxolane, both having exactly the same molecular weight and having a boiling point very close to each other, the precision distillation using a multi-stage distillation tower corresponding to a number of theoretical stages of 60 is required, and thus, it is hardly said that the production method of PTL 2 is suitable for production on an industrial scale.

The present invention relates to a method for producing a 1,3-dioxan-5-one by a short-step and simple method from raw materials that are procurable easily and inexpensively, by using a 1,3-dioxane (compound represented by the following formula (I)) that is a mixture containing a 1,3-dioxolane (compound represented by the following formula (II)) as a raw material, and furthermore, relates to an industrially advantageous production method from which DHA and serinol can be produced.

The present inventor has found that the problem is able to be solved by a production method including specified steps.

In accordance with the present invention, a 1,3-dioxan-5-one can be produced by a short-step and simple method from raw materials that are procurable easily and inexpensively, using a 1,3-dioxane that is a mixture containing a 1,3-dioxolane as a raw material. In addition, DHA and serinol can be produced from the resulting 1,3-dioxan-5-one.

[Raw Material]

In the production method of a 1,3-dioxan-5-one according to the present invention, a mixture of a compound represented by the following formula (I) and a compound represented by the following formula (II) is used as a raw material:

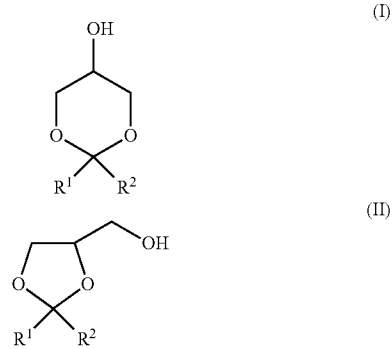

wherein, in the formulae (I) and (II), $R^1$ and $R^2$ each independently represent a hydrogen atom or a monovalent hydrocarbon group, or $R^1$ and $R^2$ are bonded to each other to form a divalent hydrocarbon group for constituting a ring structure.

In the formulae (I) and (II), $R^1$ and $R^2$ each independently represent a hydrogen atom or a monovalent hydrocarbon group, or $R^1$ and $R^2$ are bonded to each other to form a divalent hydrocarbon group for constituting a ring structure.

As a preferred embodiment of $R^1$ and $R^2$, from the viewpoint that an isomer ratio of the dioxane is high, $R^1$ is preferably a hydrogen atom, and from the viewpoints of availability of raw material, stability of the dioxanone, and separation easiness, $R^2$ is preferably a hydrogen atom or a monovalent hydrocarbon group having 1 or more and 20 or less carbon atoms. The hydrocarbon group for $R^2$ is preferably an alkyl group or an aryl group. The carbon number of the alkyl group is preferably 1 or more, and it is preferably 20 or less, more preferably 18 or less, still more preferably 16 or less, yet still more preferably 14 or less, yet still more preferably 12 or less, yet still more preferably 10 or less, yet still more preferably 8 or less, yet still more preferably 6 or less, yet still more preferably 4 or less, and yet still more preferably 2 or less. Such an alkyl group may be either linear or branched. In addition, the carbon number of the aryl group for $R^2$ is preferably 6 or more, and it is preferably 20 or less, more preferably 18 or less, still more preferably 16 or less, yet still more preferably 14 or less, yet still more preferably 12 or less, yet still more preferably 10 or less, yet still more preferably 8 or less, and yet still more preferably 6 or less. From the aforementioned viewpoint, $R^2$ is preferably a hydrogen atom or a monovalent hydrocarbon group having 1 or more and 20 or less carbon atoms, more preferably a hydrogen atom or a linear alkyl group having 1 or more and 8 or less carbon atoms, a branched alkyl group having 1 or more and 8 or less carbon atoms, or an aryl group having 6 or more and 20 or less carbon atoms, still more preferably a hydrogen atom, a methyl group, or a phenyl group, and yet still more preferably a hydrogen atom.

As another preferred embodiment of $R^1$ and $R^2$, from the viewpoints of availability of raw material and reactivity, preferably, $R^1$ is a monovalent hydrocarbon group having 1 or more and 8 or less carbon atoms, and $R^2$ is a monovalent hydrocarbon group having 1 or more and 8 or less carbon atoms; more preferably, $R^1$ is an alkyl group having 1 or more and 8 or less carbon atoms, and $R^2$ is an alkyl group having 1 or more and 8 or less carbon atoms; still more preferably, $R^1$ is an alkyl group having 1 or 2 carbon atoms, and $R^2$ is an alkyl group having 1 or more and 6 or less carbon atoms; yet still more preferably, $R^1$ is an alkyl group having 1 or 2 carbon atoms, and $R^2$ is an alkyl group having 1 or more and 4 or less carbon atoms; yet still more preferably, $R^1$ is a methyl group, and $R^2$ is a methyl group or an ethyl group; and yet still more preferably, $R^1$ is a methyl group, and $R^2$ is a methyl group.

As a still another preferred embodiment of $R^1$ and $R^2$, $R^1$ and $R^2$ are bonded to each other to form a divalent hydrocarbon group for constituting a ring structure. From the viewpoints of availability of raw material and reactivity, $R^1$ and $R^2$ are preferably bonded to each other to form a divalent hydrocarbon group having 2 or more and 7 or less carbon atoms, more preferably a divalent hydrocarbon group having 3 or more and 6 or less carbon atoms, still more preferably a divalent hydrocarbon group having 4 or more and 5 or less carbon atoms, and yet still more preferably a divalent hydrocarbon group having 5 carbon atoms. That is, the ring structure containing $R^1$ and $R^2$ is preferably a 3- to 8-membered ring, more preferably a 4- to 7-membered ring, still more preferably a 5- to 6-membered ring, and yet still more preferably a 6-membered ring. The ring structure containing $R^1$ and $R^2$ is preferably a cycloalkane structure, more preferably a ring structure having 5 or 6 carbon atoms (cyclopentane ring or cyclohexane ring), and still more preferably a cyclohexane ring.

In the formula (I), in the case where $R^1$ and $R^2$ are bonded to each other to constitute a ring structure, the formula (I) becomes the following formula (I'); and similarly, in the formula (II), in the case where $R^1$ and $R^2$ are bonded to each other to constitute a ring structure, the formula (II) becomes the following formula (II').

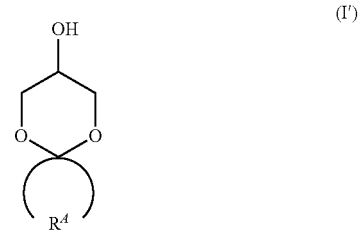

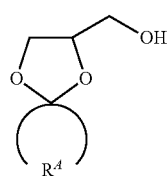

In the formulae (I') and (II'), $R^4$'s each indicate a divalent hydrocarbon group to form a ring structure.

In the formulae (I') and (II'), the ring structure containing $R^4$ is preferably a 3- to 8-membered ring, more preferably a 4- to 7-membered ring, still more preferably a 5- to 6-membered ring, and yet still more preferably a 6-membered ring. The ring structure containing $R^4$ is preferably a cycloalkane structure, and as mentioned above, it is preferred that a cyclopentane ring or a cyclohexane ring is formed, and it is more preferred that a cyclohexane ring is formed.

That is, $R^4$ is preferably an ethylene group ($—(CH_2)_2—$), a trimethylene group ($—(CH_2)_3—$), a tetramethylene group (($—(CH_2)_4—$), a pentamethylene group ($—(CH_2)_5—$), a hexamethylene group ($—(CH_2)_6—$), or a heptamethylene group ($—(CH_2)_7—$), more preferably a trimethylene group, a tetramethylene group, a pentamethylene group, or a hexamethylene group, still more preferably a tetramethylene group or a pentamethylene group, and yet still more preferably a pentamethylene group.

In the compound represented by the formula (I), in the case where $R^1$ and $R^2$ are not identical with each other, cis- and trans-isomers are existent.

In the compound represented by the formula (II), one or more asymmetric carbons are existent. In consequence, the compound represented by the formula (II) is existent as a racemate or a stereoisomer mixture unless an enantioselective reaction or separation of stereoisomers is applied.

As for the raw material of the present invention, a stereoisomer ratio of the compound represented by the formula (I) and a stereoisomer ratio of the compound represented by the formula (II) are not particularly limited.

As for the mixture of the compound represented by the formula (I) and the compound represented by the formula (II), a product that is marketed as the mixture may be used, or as mentioned later, a mixture of the compound (dioxane) represented by the formula (I) and the compound (dioxolane) represented by the formula (II) may be produced and used, and there is no particular limitation. However, from the viewpoint of inexpensive production, it is preferred that the present invention includes a step of producing a mixture of the dioxane and the dioxolane (step 1).

<Step 1: Production of Mixture of Dioxane and Dioxolane>

The method of producing the mixture of the compound (dioxane) represented by the formula (I) and the compound (dioxolane) represented by the formula (II), which is used in the present invention, is not limited, and from the viewpoints of availability of raw material, yield, and easiness of reaction operation, the mixture is preferably produced by a method of acetalizing glycerol, and a compound represented by the following formula (V) or a multimer thereof in the presence of an acid catalyst (method 1), or a method of subjecting glycerol and a compound represented by the following formula (VI) to acetal exchange in the presence of an acid catalyst (method 2), both of which are generally widely known. The resulting mixture can be used as it is, or after being purified, as the raw material in the subsequent step 2, and from the viewpoint of the yield in the step 2, the mixture is preferably purified to remove an unreacted raw material, etc., and from the viewpoint of easiness of purification, it is more preferred to perform distillation purification.

The glycerol, the compound represented by the following formula (V), and the compound represented by the following formula (VI) are available easily and inexpensively, and by adopting the method 1 or 2, it is possible to produce the raw material of the present invention easily and inexpensively.

Reaction formulae of the methods 1 and 2 are shown below.

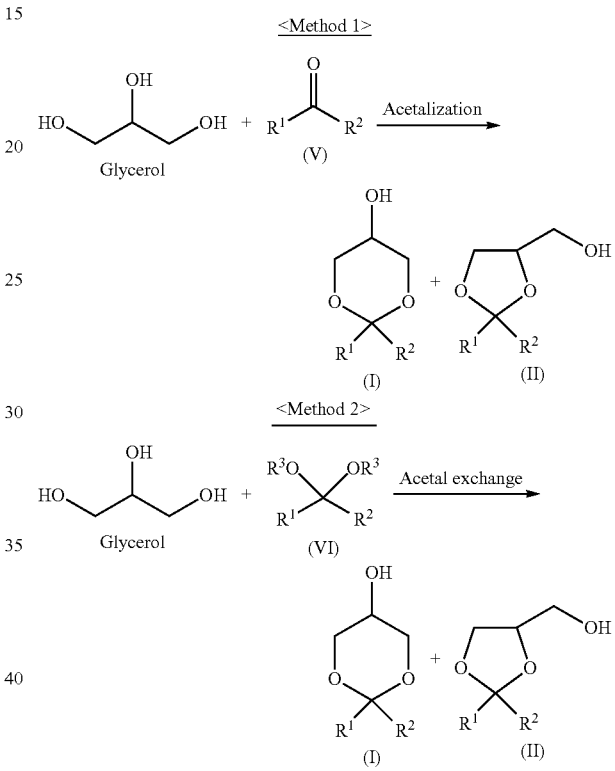

In the formulae (V) and (VI), $R^1$ and $R^2$ are synonymous with $R^1$ and $R^2$ in the formula (I) or (II), and in the formula (VI), $R^3$'s each independently represent a monovalent hydrocarbon group.

As the mixture of the dioxane and the dioxolane to be used in the present invention, any mixtures in which an isomer ratio of the dioxane is 20% or more can be used, and from the viewpoints of productivity and economy, the isomer ratio of the dioxane is preferably high as far as possible. The isomer ratio of the dioxane is preferably 30% or more, more preferably 40% or more, and still more preferably 50% or more.

In the formula (VI), $R^3$ is a monovalent hydrocarbon group, from the viewpoint of availability of raw material, $R^3$ is preferably a hydrocarbon group having 1 or more and 8 or less carbon atoms, and from the viewpoint of promoting a reaction by distilling an alcohol by-produced by the acetal exchange reaction outside the reaction system, $R^3$ is more preferably a monovalent hydrocarbon group having 1 or more and 3 or less carbon atoms, still more preferably a monovalent alkyl group having 1 or more and 3 or less carbon atoms, and yet still more preferably a methyl group.

Examples of the multimer of the compound represented by the formula (V) include paraformaldehyde that is a multimer of formaldehyde and paraldehyde (another name: 2,4,6-trimethyl-1,3,5-trioxane) that is a cyclic trimer of acetaldehyde. Taking into consideration easiness of handling, etc., the compound represented by the formula (V) or a multimer thereof may be properly chosen and used.

Production Method of 1,3-Dioxan-5-one

The production method of a 1,3-dioxan-5-one according to the present invention is a method for producing a 1,3-dioxan-5-one, including using a mixture of the compound represented by the formula (I) and the compound represented by the formula (II) as a raw material, the method including a step of oxidizing the mixture under an oxidative esterification condition (step 2).

According to the step 2, the compound represented by the formula (I) is oxidized to form a 1,3-dioxan-5-one represented by the following formula (III) (hereinafter also referred to as "dioxanone"), and the compound represented by the formula (II) is oxidatively esterified to form a compound represented by the following formula (IV) (hereinafter also referred to as "ester dimer").

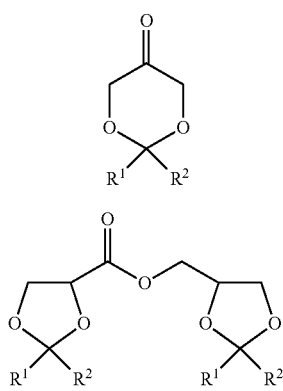

In the formulae (III) and (IV), $R^1$ and $R^2$ are synonymous with $R^1$ and $R^2$ in the formula (I) or (II).

In the dioxolane of the formula (II), since one or more asymmetric carbons are existent, the ester dimer of the formula (IV) is obtained as a stereoisomer mixture unless a dioxolane having an enantiomeric excess of 100% is used.

In the glycerin acetal, a 6-membered dioxane (compound represented by the formula (I)) and a 5-membered dioxolane (compound represented by the formula (II)) are close to each other in physical properties, such as boiling point and solubility, and separation therebetween is very difficult. In addition, oxidation mixture or deprotection mixture obtained therefrom involves the same problem. In the present invention, by adopting the oxidative esterification condition for oxidation condition of the glycerin acetal mixture to form an oxidation mixture having a large difference in physical properties, such as boiling point and solubility (mixture of the compound represented by the formula (III) (dioxanone) and the compound represented by the formula (IV) (ester dimer)), the ester dimer whose molecular weight is larger by about two times than the dioxanone becomes a by-product to be subjected to the separation, and therefore, it becomes easy to obtain the dioxanone through separation of the ester dimer. For example, a high-purity dioxanone can be easily obtained through distillation purification utilizing the matter that the difference in boiling point is large.

That is, in the step 2 according to the present invention, with respect to the mixture of the glycerin acetal (mixture of the compound represented by the formula (I) and the compound represented by the formula (II)), the dioxane (compound represented by the formula (I)) is oxidized under the condition under which the dioxolane (compound represented by the formula (II)) is oxidatively esterified, thereby producing the dioxanone (compound represented by the formula (III)) and the ester dimer (compound represented by the formula (IV)) which are large in a difference of physical properties.

<Step 2: Oxidation Reaction Under Oxidative Esterification Condition>

In the present invention, the step 2 is a step of oxidizing a mixture of a compound represented by the following formula (I) and a compound represented by the following formula (II) under an oxidative esterification condition.

In the step 2, when the mixture of the compound represented by the following formula (I) and the compound represented by the following formula (II) is oxidized under an oxidative esterification condition, the following reaction occurs.

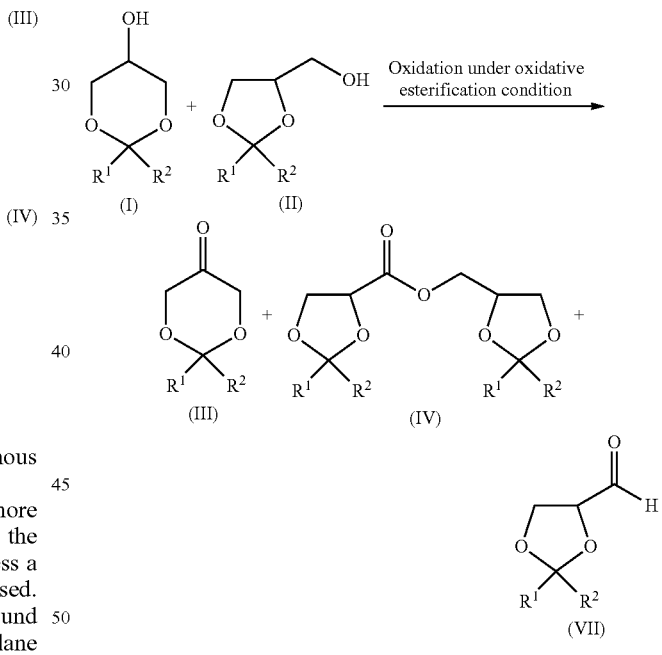

In the formulae, $R^1$ and $R^2$ are those mentioned above.

The oxidative esterification is one kind of oxidation reaction for obtaining an ester from a primary alcohol and an alcohol in a broad sense and is more generally a reaction for obtaining one molecule of an ester dimer from two molecules of the same primary alcohol, and also has another name, such as oxidative dimerization. In the present invention, the oxidative esterification means a reaction for obtaining the ester dimer (compound represented by the formula (IV)) from the dioxolane (compound represented by the formula (II)).

Examples of the method of oxidative esterification include a method of using a homogeneous or heterogeneous metal catalyst; a method of using 4-acetamido-2,2,6,6-tetramethyl-1-oxopiperidium tetrafluoroborate and pyridine, as described in Reference Literature 1 (The Journal of Organic Chemistry, Vol. 69, pp. 5116-5119, 2004); and a method of using a catalytic amount of 2,2,6,6-tetramethylpiperidine-1-oxyl (hereinafter also referred to as "TEMPO"), an oxidizing agent, and pyridine, as described in Reference Literature 2 (Synlett, Vol. 23, pp. 2261-2265, 2012).

An object of the present invention is to obtain the dioxanone (compound represented by the formula (III)) through oxidation of the dioxane (compound represented by the formula (I)). In addition, in order to easily separate the dioxanone produced by the reaction from other components, it is necessary to suppress the production amount of a compound represented by the formula (VII) (hereinafter also referred to as "formyl dioxolane") which may be produced through oxidation of the dioxolane (compound represented by the formula (II)).

Then, in the present invention, the oxidation to be performed under an oxidative esterification condition is defined as the oxidation method satisfying the following three conditions.

Condition 1: The dioxanone is produced from the dioxane.

Condition 2: The ester dimer is produced from the dioxolane.

Condition 3: The yield of the formyl dioxolane produced from the dioxolane is 10% or less and 0% or more.

In the present invention, any oxidation methods satisfying the aforementioned definition can be adopted, and oxidation methods preferred from the viewpoint of obtaining high reaction activity are selected from an oxidation method of using a salt containing an oxo ammonium cation of an organic nitroxyl radical and a base, as in Reference Literature 1; and an oxidation method of using a compound selected from an organic nitroxyl radical, an N-hydroxy form thereof, and a salt containing an oxo ammonium cation of them, an oxidizing agent, and a base (hereinafter also referred to as "nitroxyl radical method"), as in Reference Literature 2. From the viewpoint that the yields of the dioxanone and the ester dimer are high and the yield of the formyl dioxolane is low, the nitroxyl radical method is preferred. Above all, the oxidation method of using an organic nitroxyl radical and/or an N-hydroxy form thereof, an oxidizing agent, and a base is more preferred.

(Nitroxyl Radical Method)

[Nitroxyl Radical Species]

In the present reaction, as the nitroxyl radical speltles, a compound selected from an organic nitroxyl radical, an N-hydroxy form thereof, and a salt containing an oxo ammonium cation of them, all of which have oxidation activity with the dioxane and the dioxolane through a combination with an oxidizing agent, can be used.

That is, as the nitroxyl radical species, it is preferred to use at least one compound selected from an organic nitroxyl radical, an N-hydroxy form thereof, and a salt containing an oxo ammonium cation of them.

From the viewpoint that high oxidation activity is obtained, the organic nitroxyl radical is preferably a compound represented by the following formula (VIII), a compound represented by the following formula (IX), or a compound represented by the following formula (X). That is, the nitroxyl radical species is preferably a compound selected from a compound represented by the following formula (VIII), a compound represented by the following formula (IX), or a compound represented by the following formula (X), an N-hydroxy form of them, and a salt containing an oxo ammonium cation of them.

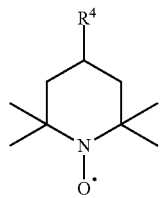

(VIII)

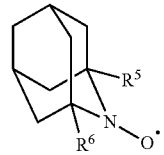

(IX)

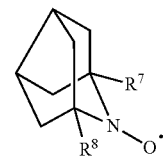

(X)

In the formula (VIII), $R^4$ represents a hydrogen atom, a halogen atom, a hydroxy group, an alkoxy group, an acyloxy group, an alkoxycarbonyl group, an amino group, an acylamino group, a sulfonyloxy group, an N-alkylcarbamoyloxy group, a carboxy group, a cyano group, an isocyanato group, an isothiocyanato group, or an oxo group. In the formula (IX), $R^5$ and $R^6$ each independently represent a hydrogen atom or a methyl group. In the formula (X), $R^7$ and $R^8$ each independently represent a hydrogen atom or a methyl group.

In the formula (VIII), $R^4$ represents a hydrogen atom, a halogen atom, a hydroxy group (—OH), an alkoxy group, an acyloxy group, an alkoxycarbonyl group, an amino group, an acylamino group, a sulfonyloxy group, an N-alkylcarbamoyloxy group, a carboxy group (—C(=O)—OH), a cyano group (—C≡N), an isocyanato group (—N=C=O), an isothiocyanato group (—N=C=S), or an oxo group (=O). In the formula (VIII), from the viewpoint of availability and obtaining the dioxanone in a high yield, $R^4$ is preferably an alkoxy group, an acyloxy group, or an acylamino group.

Examples of the halogen atom include a fluorine atom, a chlorine atom, a bromine atom, and an iodine atom, and from the viewpoints of easy availability or preparation and low molecular weight, a fluorine atom, a chlorine atom, or a bromine atom is preferred.

The alkoxy group is represented by —$OR^9$, and $R^9$ represents a monovalent hydrocarbon group. From the viewpoints of easy availability or preparation and low molecular weight, $R^9$ is preferably an alkyl group having 1 to 12 carbon atoms, an alkenyl group having 2 to 12 carbon atoms, an alkynyl group having 2 to 12 carbon atoms, or an aryl group having 6 to 20 carbon atoms; more preferably an alkyl group having 1 to 6 carbon atoms, an alkenyl group having 2 to 6 carbon atoms, an alkynyl group having 2 to 6 carbon atoms, or an aryl group having 6 to 14 carbon atoms; still more preferably an alkyl group having 1 to 4 carbon atoms, an alkenyl group having 2 to 4 carbon atoms, an alkynyl group having 2 to 4 carbon atoms, or an aryl group having 6 to 10 carbon atoms; and yet still more preferably a methyl group. In $R^9$, a part of the hydrogen atoms may be substituted with a halogen atom.

The acyloxy group is represented by —O(C=O)—R$^{10}$. From the viewpoints of easy availability or preparation and low molecular weight, R$^{10}$ is preferably a hydrogen atom, an alkyl group having 1 to 12 carbon atoms, an alkenyl group having 1 to 12 carbon atoms, or an aryl group having 6 to 20 carbon atoms; more preferably a hydrogen atom, an alkyl group having 1 to 8 carbon atoms, or an aryl group having 6 to 14 carbon atoms; still more preferably a hydrogen atom, an alkyl group having 1 to 4 carbon atoms, or an aryl group having 6 to 10 carbon atoms; yet still more preferably a methyl group, an ethyl group, or a phenyl group; and even yet still more preferably a phenyl group.

The acylamino group is represented by —NH(C=O)—R$^{11}$. From the viewpoints of easy availability or preparation and low molecular weight, R$^{11}$ is preferably a hydrogen atom, an alkyl group having 1 to 12 carbon atoms, or an aryl group having 6 to 20 carbon atoms; more preferably a hydrogen atom, an alkyl group having 1 to 8 carbon atoms, or an aryl group having 6 to 14 carbon atoms; still more preferably a hydrogen atom, an alkyl group having 1 to 4 carbon atoms, or an aryl group having 6 to 10 carbon atoms; yet still more preferably a methyl group, an ethyl group, or a phenyl group; and even yet still more preferably a methyl group.

The sulfonyloxy group is represented by —O(O=S=O)—R$^{12}$. From the viewpoints of easy availability or preparation and low molecular weight, R$^{12}$ is preferably an alkyl group having 1 to 12 carbon atoms or an aryl group having 6 to 20 carbon atoms; more preferably an alkyl group having 1 to 8 carbon atoms or an aryl group having 6 to 14 carbon atoms; still more preferably an alkyl group having 1 to 4 carbon atoms or an aryl group having 6 to 10 carbon atoms; yet still more preferably a methyl group, an ethyl group, or a p-tolyl group; and even yet still more preferably a methyl group or a p-tolyl group.

Specifically, examples of the nitroxyl radical species include TEMPO, 4-hydroxy-TEMPO, 4-amino-TEMPO, 4-methoxy-TEMPO (hereinafter also referred to as "4-OMe-TEMPO"), 4-ethoxy-TEMPO, 4-phenoxy-TEMPO, 4-acetoxy-TEMPO, 4-benzoyloxy-TEMPO (hereinafter also referred to as "4-OBz-TEMPO"), 4-methacrylate-TEMPO, 4-acetamido-TEMPO (hereinafter also referred to as "4-NHAc-TEMPO"), 4-methylsulfonyloxy-TEMPO (hereinafter also referred to as "4-OMs-TEMPO"), 4-p-toluenesulfonyloxy-TEMPO, 4-oxo-TEMPO, 2-azaadamantane-N-hydroxyl (hereinafter also referred to as "AZADOL" (a trademark, manufactured by Nissan Chemical Industries, Ltd.)), 2-azaadamantane-N-oxyl (hereinafter also referred to as "AZADO"), 1-methyl-2-azaadamantane-N-oxyl (hereinafter also referred to as "1-Me-AZADO"), 9-azanoradamantane-N-oxyl (hereinafter also referred to as "nor-AZADO"), and 1,5-dimethyl-9-azanoradamantane-N-oxyl (hereinafter also referred to as "DMM-AZADO").

From the viewpoints of availability and obtaining the dioxanone in a high yield, the nitroxyl radical species is preferably a compound selected from 4-methoxy-TEMPO, 4-benzoyloxy-TEMPO, 4-acetamido-TEMPO, 4-methylsulfonyloxy-TEMPO, and AZADOL, and more preferably a compound selected from 4-benzoyloxy-TEMPO, 4-acetamido-TEMPO, 4-methylsulfonyloxy-TEMPO, and AZADOL.

Though preferred compounds are hereunder exemplified, in the present invention, it should be construed that the nitroxyl radical species is not limited to these compounds.

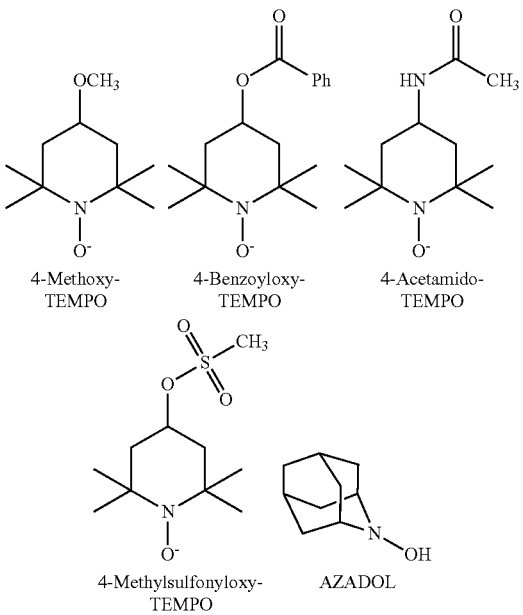

4-Methoxy-TEMPO    4-Benzoyloxy-TEMPO    4-Acetamido-TEMPO

4-Methylsulfonyloxy-TEMPO    AZADOL

From the viewpoint of securing satisfactory oxidation activity, a use amount of the compound selected from an organic nitroxyl radical, an N-hydroxy form thereof, and a salt containing an oxo ammonium cation of them is preferably 0.0001 or more in a molar ratio, more preferably 0.0002 or more in a molar ratio, and still more preferably 0.0005 or more in a molar ratio relative to the mixture of the dioxane and dioxolane. In addition, from the viewpoint of economy, it is preferably 0.1 or less in a molar ratio, more preferably 0.05 or less in a molar ratio, and still more preferably 0.02 or less in a molar ratio.

[Oxidizing Agent]

In the present reaction, from the viewpoint of reactivity, an oxidizing agent is used together with the nitroxyl radical species. Any oxidizing agent capable of oxidizing the organic nitroxyl radical or an N-hydroxy form thereof into an oxo ammonium cation can be used as the oxidizing agent, and from the viewpoint of suppressing a lowering of the yield due to hydration or hydrolysis of the dioxanone or ester dimer, an oxidizing agent composed of a compound containing a halogen, which is capable of being used in an organic solvent (hereinafter also referred to as "halogen-containing oxidizing agent"), is preferred. Examples of the halogen-containing oxidizing agent include an oxidizing agent composed of a compound containing chlorine (hereinafter also referred to as "chlorine-containing oxidizing agent"), such as sodium hypochlorite pentahydrate, meta-chloroperbenzoic acid, trichloroisocyanuric acid (hereinafter also referred to as "TCCA"), tertiary butyl hypochlorite (hereinafter also referred to as "$^t$BuOCl"), and N-chlorosuccinimide; an oxidizing agent composed of a compound containing bromine (hereinafter also referred to as "bromine-containing oxidizing agent"), such as N-bromosuccinimide; and a halogen-containing oxidizing agent having plural halogen elements, such as (dichloroiodo) benzene. From the viewpoint of obtaining the ester dimer of the present invention in a high yield and the viewpoints of stability, safety, and easiness of handling of the oxidizing agent, the halogen-containing oxidizing agent is preferably a chlorine-containing oxidizing agent, and more preferably an oxidizing agent selected from TCCA and $^t$BuOCl, with TCCA being still more preferred from the viewpoint of availability.

As the oxidizing agent of the present invention, an oxoammonium cation of an organic nitroxyl radical or an N-hydroxy form thereof, including an oxoammonium cation resulting from one electron oxidation of the compound represented by the formula (VIII), the compound represented by the formula (IX), or the compound represented by the formula (X), is excluded.

From the viewpoints of making both high reaction conversion of the mixture of the dioxane and the dioxolane and suppression of production amount of the formyl dioxolane compatible with each other, a molar ratio of the oxidation active species relative to the mixture of the dioxane and the dioxolane is preferably 1.0 or more, and more preferably 1.1 or more. In addition, from the viewpoints of economy and reduction of waste amount, the molar ratio is preferably 2.0 or less, and more preferably 1.5 or less.

The oxidation active species means a chlorine atom in the case of the chlorine-containing oxidizing agent, and in the case of TCCA, 3 moles of the oxidation active species is existent in one mole of the molecule.

[Base]

In the present reaction, a base is used for the purpose of neutralizing an acid by-produced due to consumption of the oxidizing agent, or other purpose. Any base can be used unless it directly causes a side-reaction with the mixture of the dioxane and the dioxolane, the catalyst, or the oxidizing agent to impair the target oxidation reaction, and a heterocyclic aromatic amine having a pyridine skeleton is preferred from the viewpoints that it is weakly basic and that a side-reaction is suppressed. For the purpose of suppressing the use amount, the heterocyclic aromatic amine having a pyridine skeleton may be used in combination with an inorganic base, and from the viewpoint of obtaining the dioxanone in a high yield, the heterocyclic aromatic amine having a pyridine skeleton is preferably used alone.

Examples of the heterocyclic aromatic amine having a pyridine skeleton include pyridine, an alkyl-substituted pyridine, a polycyclic quinoline, and a bipyridyl that is a pyridine dimer. Specifically, examples thereof include pyridine, 2-methylpyridine, 3-methylpyridine, 4-methylpyridine, 2-ethylpyridine, 3-ethylpyridine, 4-ethylpyridine, 2,6-lutidine, 3,5-lutidine, 2,3,5-collidine, 2,4,6-collidine, 5-ethyl-2-methylpyridine, 3,5-diethylpyridine, 2,2'-bipyridyl, 2,4'-bipyridyl, 4,4'-bipyridyl, and quinoline.

Among the heterocyclic aromatic amines having a pyridine skeleton, it is preferred to select and use a heterocyclic aromatic amine having a pyridine skeleton, which is large in a difference of boiling point from the dioxanone and which is easily separated through distillation. From the viewpoint of availability, an amine selected from pyridine and 5-ethyl-2-methylpyridine is preferred; from the viewpoint of easiness of recovery on regenerating an amine from an amine salt after completion of the reaction, a water-insoluble heterocyclic aromatic amine having a pyridine skeleton is preferred; and from the viewpoint of yield, an amine selected from pyridine, 3,5-lutidine, 2,6-lutidine, 3-ethylpyridine, 4-ethylpyridine, and 5-ethyl-2-methylpyridine is preferred, and an amine selected from pyridine, 3,5-lutidine, 3-ethylpyridine, 4-ethylpyridine, and 5-ethyl-2-methylpyridine is more preferred.

From the viewpoint of completely neutralizing an oxidizing agent-derived acid to suppress the decomposition of an acetal group of the dioxane and the dioxolane, a molar ratio of the base relative to the mixture of the dioxane and the dioxolane is preferably 1.0 or more, more preferably 1.1 or more, still more preferably 1.2 or more, and yet still more preferably 1.3 or more. In addition, from the viewpoints of economy and easiness of recovery of the excessive base, the molar ratio is preferably 2.5 or less, more preferably 2.0 or less, and still more preferably 1.7 or less.

[Solvent]

In the present reaction, it is possible to carry out the reaction under a non-solvent or solvent-used condition. In the case where the oxidizing agent to be used or an oxidizing agent-derived reduced product or salt, which is by-produced at the time of reaction, is a solid, from the viewpoints of dissolving the solid and decreasing the viscosity of the reaction solution to make it easy to perform stirring, the solvent-used condition is preferred. Any solvent can be used so far as it is inert against the mixture of the dioxane and the dioxolane, the oxidizing agent, and the base, and in the case of using TCCA as the oxidizing agent, from the viewpoint of solubility of TCCA and availability, a solvent selected from acetone, 2-butanone, cyclopentanone, acetonitrile, and dichloromethane is preferred; a solvent selected from acetone, 2-butanone, acetonitrile, and dichloromethane is more preferred; and a solvent selected from acetone and 2-butanone is still more preferred. In addition, from the viewpoint of productivity of the dioxanone of the present invention, acetonitrile is still more preferred.

The solvent may be used alone or may be used in combination of two or more thereof.

The use amount of the solvent is not particularly limited, and from the viewpoint of operability and the viewpoint of obtaining the dioxanone in a high yield, the use amount of the solvent relative to the whole of the reaction system is preferably 20% by mass or more, more preferably 30% by mass or more, still more preferably 40% by mass or more, yet still more preferably 50% by mass or more, and even yet still more preferably 60% by mass or more, and from the viewpoint of productivity, the use amount of the solvent relative to the whole of the reaction system is preferably 90% by mass or less, more preferably 85% by mass or less, and still more preferably 80% by mass or less.

[Reaction Procedures]

In the present reaction, the charging order of the respective raw materials, and the like are not limited, since the reaction is an exothermic oxidation reaction, from the viewpoints of easiness of temperature control of the reaction solution and safety, a method of dropping the oxidizing agent or oxidizing agent solution to the mixture or the mixed solution containing the raw materials other than the oxidizing agent is preferred.

From the viewpoint of suppressing a facility load and a rise of viscosity of the reaction solution, a temperature of the reaction solution during dropping of the oxidizing agent or oxidizing agent solution is preferably −15° C. or higher, and more preferably −10° C. or higher. In addition, from the viewpoint of suppressing a side-reaction, such as decomposition at a high temperature, to obtain the dioxanone in a high yield, the temperature of the reaction solution is preferably 25° C. or lower, and more preferably 10° C. or lower. After completion of dropping of the oxidizing agent or oxidizing agent solution, the reaction is continued until the dioxane and the dioxolane all react, or a lowering of the residual amount stops. From the viewpoint of promoting the reaction of the dioxane, the temperature of the reaction solution is preferably −10° C. or higher, and more preferably −5° C. or higher, and from the viewpoint of suppressing a side-reaction, it is preferably 50° C. or lower, and more preferably 30° C. or lower.

At the time of completion of the reaction, from the viewpoints of suppression of a side-reaction and safety, it is preferred to add a reaction terminator that completely consumes the residual oxidizing agent. As the reaction terminator, any compound can be used so far as it reacts with the oxidizing agent and hardly reacts with the oxidation product, such as the dioxanone, and; however, from the viewpoints of availability and making it easy to purify the dioxanone, an alcohol is preferred. The alcohol is preferably a primary or secondary alcohol, and from the viewpoint of suppressing ester interchange with the ester dimer, the alcohol is more preferably a secondary alcohol. In addition, an alcohol having 1 or more and 12 or less carbon atoms is preferred.

The addition amount of the reaction terminator is not particularly limited.

<Step 3: Separation and Purification of Dioxanone>

In the present invention, it is preferred to include, after the step 2, a step of separating the 1,3-dioxan-5-one (dioxanone that is the compound represented by the formula (III)) (step 3). The dioxanone is purified by the step 0.

In the step 3, from the viewpoint of efficiency, it is preferred that the solid, such as the salt or the reduced product of the oxidizing agent, is separated by means of filtration or oil-water extraction, and that the ester dimer, the formyl dioxolane, and the residual base are separated by means of distillation or column chromatography.

For the separation between the dioxanone and the ester dimer, from the viewpoint of making it possible to easily perform the separation utilizing a large difference in boiling point, the separation by means of distillation is more preferred.

It is possible to carry out the separation by means of distillation under either simple distillation conditions or rectification conditions, and from the viewpoint of obtaining the high-purity dioxanone in a high distillation yield, it is preferred to perform the separation under rectification conditions. As for the rectification conditions, from the viewpoint of highly purifying the dioxanone, the number of theoretical stages of a rectifying tower is preferably 2 stages or more, and more preferably 5 stages or more, and a reflux ratio is preferably 0.1 or more, and more preferably 0.5 or more. In addition, from the viewpoint of productivity of dioxanone purification, the number of theoretical stages of the rectifying tower is preferably 20 stages or less, and more preferably 10 stages or less, and the reflux ratio is preferably 20 or less, and more preferably 10 or less.

[Production Method of Dihydroxyacetone]

The thus-obtained dioxanone is important as a synthetic intermediate for various useful compounds, and for example, the dihydroxyacetone can be produced through deacetalization of the dioxanone separated by the step 3.

The deacetalization of the dioxanone can be performed through hydrolysis, and specifically, examples thereof include a method of hydrolyzing the dioxanone in the presence of water and an acid (for example, hydrochloric acid and a strongly acidic cation exchange resin), as described in NPL 1 and Reference Literature 3 (Chemical Engineering Journal, Vol. 229, pp. 234-238, 2013).

The dihydroxyacetone may be used without being purified or may be used after being purified. In the case of using the dihydroxyacetone after being purified, it may be purified according to the ordinary method. Examples thereof include a method in which the aldehyde or ketone is removed through organic solvent extraction, etc., and the residue is then recrystallized from the water-ethanol mixed solution, as described in NPL 1.

Production Method of 5-Amino-1,3-Dioxane (Serinol Protective Form)

The 5-amino-1,3-dioxane (serinol protective form) represented by the following formula (XI) can be produced by subjecting the thus-obtained dioxanone to reductive amination.

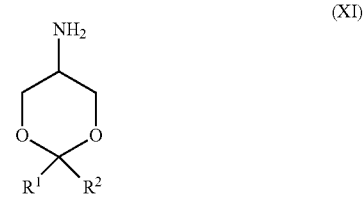

(XI)

In the formula (XI), $R^1$ and $R^2$ are synonymous with $R^1$ and $R^2$ in the formula (I) or (II).

For example, the method of subjecting the dioxanone to reductive amination is exemplified in the method described in NPL 2. Specifically, there is exemplified a method in which the dioxanone is added to an anhydrous ammonia-ethanol solution, a palladium-on-carbon is added as a catalyst, and the contents are allowed to react with each other in a hydrogen atmosphere. In addition, there are also exemplified a method of using ammonium formate as a hydrogen source and an ammonia source; and a method in which after performing reductive amination with benzylamine as an amine, the benzyl group is removed.

In the case of producing the serinol protective form by subjecting the dioxanone obtained in the step 2 to reductive amination without separating the dioxanone and the ester dimer from each other, the serinol protective form can be separated and purified by the same method as in the step 3.

Production Method of 2-Amino-1,3-propanediol (Serinol)

The serinol can be produced by subjecting the thus-obtained dioxanone to reductive amination to produce the 5-amino-1,3-dioxane, followed by deacetalization.

As a method of subjecting the dioxanone to reductive amination, the aforementioned method is exemplified.

Examples of the deacetalization include a method of hydrolyzing the 5-amino-1,3-dioxane in the presence of water and an acid (for example, hydrochloric acid), as described in Reference Literature 4 (European Patent No. 0643055).

In the case of using the 2-amino-1,3-propanediol after being purified, the purification may be performed according to the ordinary method. Examples thereof include a method in which after hydrolysis, the water is distilled off, and the residue is recrystallized from acetone, to obtain a hydrochloride of 2-amino-1,3-propanediol, as described in Reference Literature 4.

The 1,3-dioxan-5-one obtained by the present invention is important as a synthetic intermediate for various useful compounds and is suitably used for production of medicaments, chemical products, and the like.

The present invention further discloses the following [1] to [39].

[1] A method for producing a 1,3-dioxan-5-one, including using a mixture of a compound represented by the following formula (I) and a compound represented by the following formula (II) as a raw material, the method including a step of oxidizing the mixture under an oxidative esterification condition (step 2):

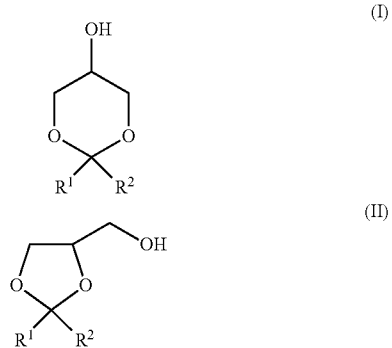

wherein, in the formulae (I) and (II), $R^1$ and $R^2$ each independently represent a hydrogen atom or a monovalent hydrocarbon group, or $R^1$ and $R^2$ are bonded to each other to form a divalent hydrocarbon group for constituting a ring structure.

[2] The method for producing a 1,3-dioxan-5-one as set forth in [1], wherein in the formulae (I) and (II), $R^1$ is a hydrogen atom.

[3] The method for producing a 1,3-dioxan-5-one as set forth in [1], wherein in the formulae (I) and (II), $R^1$ is preferably a hydrogen atom; $R^2$ is preferably a hydrogen atom or a monovalent hydrocarbon group having 1 or more and 20 or less carbon atoms; the hydrocarbon group for $R^2$ is preferably an alkyl group or an aryl group; the carbon number of the alkyl group is preferably 1 or more, and it is preferably 20 or less, more preferably 18 or less, still more preferably 16 or less, yet still more preferably 14 or less, yet still more preferably 12 or less, yet still more preferably 10 or less, yet still more preferably 8 or less, yet still more preferably 6 or less, yet still more preferably 4 or less, and yet still more preferably 2 or less; such an alkyl group may be either linear or branched; the carbon number of the aryl group for $R^2$ is preferably 6 or more, and it is preferably 20 or less, more preferably 18 or less, still more preferably 16 or less, yet still more preferably 14 or less, yet still more preferably 12 or less, yet still more preferably 10 or less, yet still more preferably 8 or less, and yet still more preferably 6 or less; and $R^2$ is preferably a hydrogen atom or a monovalent hydrocarbon group having 1 or more and 20 or less carbon atoms, more preferably a hydrogen atom or a linear alkyl group having 1 or more and 8 or less carbon atoms, a branched alkyl group having 1 or more and 8 or less carbon atoms, or an aryl group having 6 or more and 20 or less carbon atoms, still more preferably a hydrogen atom, a methyl group, or a phenyl group, and yet still more preferably a hydrogen atom.

[4] The method for producing a 1,3-dioxan-5-one as set forth in [1], wherein the formulae (I) and (II), preferably, $R^1$ is a monovalent hydrocarbon group having 1 or more and 8 or less carbon atoms, and $R^2$ is a monovalent hydrocarbon group having 1 or more and 8 or less carbon atoms; more preferably, $R^1$ is an alkyl group having 1 or more and 8 or less carbon atoms, and $R^2$ is an alkyl group having 1 or more and 8 or less carbon atoms; still more preferably, $R^1$ is an alkyl group having 1 or 2 carbon atoms, and $R^2$ is an alkyl group having 1 or more and 6 or less carbon atoms; yet still more preferably, $R^1$ is an alkyl group having 1 or 2 carbon atoms, and $R^2$ is an alkyl group having 1 or more and 4 or less carbon atoms; yet still more preferably, $R^1$ is a methyl group, and $R^2$ is a methyl group or an ethyl group; and yet still more preferably, $R^1$ is a methyl group, and $R^2$ is a methyl group.

[5] The method for producing a 1,3-dioxan-5-one as set forth in [1], wherein in the formulae (I) and (II), $R^1$ and $R^2$ are bonded to each other to form a divalent hydrocarbon group for constituting a ring structure; $R^1$ and $R^2$ are preferably bonded to each other to form a divalent hydrocarbon group having 2 or more and 7 or less carbon atoms, more preferably a divalent hydrocarbon group having 3 or more and 6 or less carbon atoms, still more preferably a divalent hydrocarbon group having 4 or more and 5 or less carbon atoms, and yet still more preferably a divalent hydrocarbon group having 5 carbon atoms; the ring structure containing $R^1$ and $R^2$ is preferably a 3- to 8-membered ring, more preferably a 4- to 7-membered ring, still more preferably a 5- to 6-membered ring, and yet still more preferably a 6-membered ring; and the ring structure containing $R^1$ and $R^2$ is preferably a cycloalkane structure, more preferably a ring structure having 5 or 6 carbon atoms (cyclopentane ring or cyclohexane ring), and still more preferably a cyclohexane ring.

[6] The method for producing a 1,3-dioxan-5-one as set forth in any of [1] to [5], wherein the mixture of a compound represented by the following formula (I) and a compound represented by the following formula (II) is produced by a method of acetalizing glycerol, and a compound represented by the following formula (V) or a multimer thereof in the presence of an acid catalyst (method 1), or a method of subjecting glycerol and a compound represented by the following formula (VI) to acetal exchange in the presence of an acid catalyst (method 2):

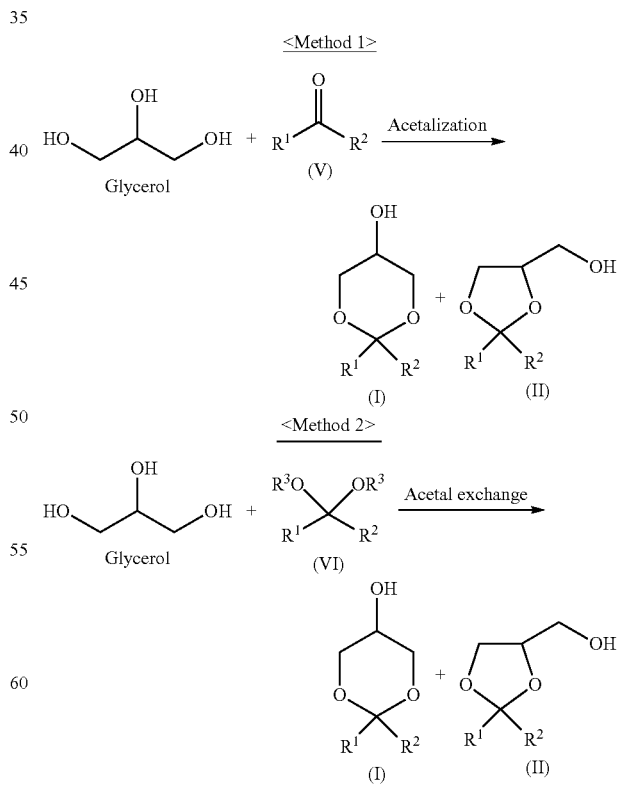

In the formulae (V) and (VI), $R^1$ and $R^2$ each independently represent a hydrogen atom or a monovalent hydrocarbon group, or R¹ and R² are bonded to each other to form a divalent hydrocarbon group for constituting a ring structure. In the formula (VI), R³'s each independently represent a monovalent hydrocarbon group, preferably a group selected from hydrocarbon groups having 1 or more and 8 or less carbon atoms, more preferably a monovalent hydrocarbon group having 1 or more and 3 or less carbon atoms, still more preferably a monovalent alkyl group having 1 or more and 3 or less carbon atoms, and yet still more preferably a methyl group.

[7] The method for producing a 1,3-dioxan-5-one as set forth in [6], wherein in the formulae (V) and (VI), R¹ is a hydrogen atom.

[8] The method for producing a 1,3-dioxan-5-one as set forth in [6], wherein in the formulae (V) and (VI), R¹ is preferably a hydrogen atom; R² is preferably a hydrogen atom or a monovalent hydrocarbon group having 1 or more and 20 or less carbon atoms; the hydrocarbon group for R² is preferably an alkyl group or an aryl group; the carbon number of the alkyl group is preferably 1 or more, and it is preferably 20 or less, more preferably 18 or less, still more preferably 16 or less, yet still more preferably 14 or less, yet still more preferably 12 or less, yet still more preferably 10 or less, yet still more preferably 8 or less, yet still more preferably 6 or less, yet still more preferably 4 or less, and yet still more preferably 2 or less; such an alkyl group may be either linear or branched; the carbon number of the aryl group for R² is preferably 6 or more, and it is preferably 20 or less, more preferably 18 or less, still more preferably 16 or less, yet still more preferably 14 or less, yet still more preferably 12 or less, yet still more preferably 10 or less, yet still more preferably 8 or less, and yet still more preferably 6 or less; and R² is preferably a hydrogen atom or a monovalent hydrocarbon group having 1 or more and 20 or less carbon atoms, more preferably a hydrogen atom or a linear alkyl group having 1 or more and 8 or less carbon atoms, a branched alkyl group having 1 or more and 8 or less carbon atoms, or an aryl group having 6 or more and 20 or less carbon atoms, still more preferably a hydrogen atom, a methyl group, or a phenyl group, and yet still more preferably a hydrogen atom.

[9] The method for producing a 1,3-dioxan-5-one as set forth in [6], wherein in the formulae (V) and (VI), preferably, R¹ is a monovalent hydrocarbon group having 1 or more and 8 or less carbon atoms, and R² is a monovalent hydrocarbon group having 1 or more and 8 or less carbon atoms; more preferably, R¹ is an alkyl group having 1 or more and 8 or less carbon atoms, and R² is an alkyl group having 1 or more and 8 or less carbon atoms; still more preferably, R¹ is an alkyl group having 1 or 2 carbon atoms, and R² is an alkyl group having 1 or more and 6 or less carbon atoms; yet still more preferably, R¹ is an alkyl group having 1 or 2 carbon atoms, and R² is an alkyl group having 1 or more and 4 or less carbon atoms; yet still more preferably, R¹ is a methyl group, and R² is a methyl group or an ethyl group; and yet still more preferably, R¹ is a methyl group, and R² is a methyl group.

[10] The method for producing a 1,3-dioxan-5-one as set forth in [6], wherein in the formulae (V) and (VI), R¹ and R² are bonded to each other to form a divalent hydrocarbon group for constituting a ring structure; R¹ and R² are preferably bonded to each other to form a divalent hydrocarbon group having 2 or more and 7 or less carbon atoms, more preferably a divalent hydrocarbon group having 3 or more and 6 or less carbon atoms, still more preferably a divalent hydrocarbon group having 4 or more and 5 or less carbon atoms, and yet still more preferably a divalent hydrocarbon group having 5 carbon atoms; the ring structure containing R¹ and R² is preferably a 3- to 8-membered ring, more preferably a 4- to 7-membered ring, still more preferably a 5- to 6-membered ring, and yet still more preferably a 6-membered ring; and the ring structure containing R¹ and R² is preferably a cycloalkane structure, more preferably a ring structure having 5 or 6 carbon atoms (cyclopentane ring or cyclohexane ring), and still more preferably a cyclohexane ring.

[11] The method for producing a 1,3-dioxan-5-one as set forth in [1] to [10], wherein in the step 2, an oxidation method selected from an oxidation method of using a salt containing an oxo ammonium cation of an organic nitroxyl radical and a base; and an oxidation method of using a compound selected from an organic nitroxyl radical, an N-hydroxy form thereof, and a salt containing an oxo ammonium cation of them, an oxidizing agent, and a base (hereinafter also referred to as "nitroxyl radical method") is preferably adopted.

[12] The method for producing a 1,3-dioxan-5-one as set forth in [1] to [11], wherein in the step 2, an oxidation method of using at least one compound selected from an organic nitroxyl radical, an N-hydroxy form thereof, and a salt containing an oxo ammonium cation of them, an oxidizing agent, and a base (nitroxyl radical method) is adopted.

[13] The method for producing a 1,3-dioxan-5-one as set forth in [11] or [12], wherein the organic nitroxyl radical is a compound represented by the following formula (VIII), a compound represented by the following formula (IX), or a compound represented by the following formula (X).

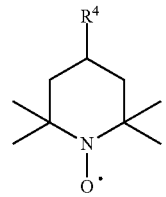

(VIII)

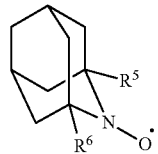

(IX)

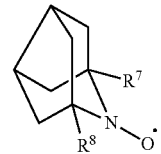

(X)

In the formula (VIII), R⁴ represents a hydrogen atom, a halogen atom, a hydroxy group, an alkoxy group, an acyloxy group, an alkoxycarbonyl group, an amino group, an acylamino group, a sulfonyloxy group, an N-alkylcarbamoyloxy group, a carboxy group, a cyano group, an isocyanato group, an isothiocyanato group, or an oxo group, preferably an alkoxy group, an acyloxy group, or an acylamino group. In the formula (IX), R⁵ and R⁶ each independently represent a hydrogen atom or a methyl group. In the formula (X), R⁷ and R⁸ each independently represent a hydrogen atom or a methyl group.

[14] The method for producing a 1,3-dioxan-5-one as set forth in any of [11] to [13], wherein at least one compound selected from the organic nitroxyl radical, an N-hydroxy form thereof, and a salt containing an oxo ammonium cation of them is preferably TEMPO, 4-hydroxy-TEMPO, 4-amino-TEMPO, 4-methoxy-TEMPO (hereinafter also referred to as "4-OMe-TEMPO"), 4-ethoxy-TEMPO, 4-phenoxy-TEMPO, 4-acetoxy-TEMPO, 4-benzoyloxy-TEMPO (hereinafter also referred to as "4-OBz-TEMPO"), 4-methacrylate-TEMPO, 4-acetamido-TEMPO (hereinafter also referred to as "4-NHAc-TEMPO"), 4-methylsulfonyloxy-TEMPO (hereinafter also referred to as "4-OMs-TEMPO"), 4-p-toluenesulfonyloxy-TEMPO, 4-oxo-TEMPO, 2-azaadamantane-N-hydroxy (hereinafter also referred to as "AZADOL"), 2-azaadamantane-N-oxyl (hereinafter also referred to as "AZADO"), 1-methyl-2-azaadamantane-N-oxyl (hereinafter also referred to as "1-Me-AZADO"), 9-azanoradamantane-N-oxyl (hereinafter also referred to as "nor-AZADO"), or 1,5-dimethyl-9-azanoradamantane-N-oxyl (hereinafter also referred to as "DMM-AZADO"); more preferably a compound selected from 4-methoxy-TEMPO, 4-benzoyloxy-TEMPO, 4-acetamido-TEMPO, 4-methylsulfonyloxy-TEMPO, and AZADOL; and still more preferably a compound selected from 4-benzoyloxy-TEMPO, 4-acetamido-TEMPO, 4-methylsulfonyloxy-TEMPO, and AZADOL.

[15] The method for producing a 1,3-dioxan-5-one as set forth in any of [12] to [14], wherein a use amount of the compound selected from the organic nitroxyl radical, an N-hydroxy form thereof, and a salt containing an oxo ammonium cation of them is preferably 0.0001 or more in a molar ratio, more preferably 0.0002 or more in a molar ratio, and still more preferably 0.0005 or more in a molar ratio, and it is preferably 0.1 or less in a molar ratio, more preferably 0.05 or less in a molar ratio, and still more preferably 0.02 or less in a molar ratio, relative to the mixture of the compound represented by the formula (I) and the compound represented by the formula (II).

[16] The method for producing a 1,3-dioxan-5-one as set forth in any of [11] to [15], wherein the oxidizing agent is preferably an oxidizing agent composed of a compound containing a halogen (halogen-containing oxidizing agent), more preferably an oxidizing agent composed of a compound containing chlorine (chlorine-containing oxidizing agent), still more preferably an oxidizing agent selected from trichloroisocyanuric acid and tertiary butyl hypochlorite, and yet still more preferably trichloroisocyanuric acid.

[17] The method for producing a 1,3-dioxan-5-one as set forth in any of [11] to [16], wherein a molar ratio of the oxidation active species of the oxidizing agent relative to the mixture of the compound represented by the formula (I) and the compound represented by the formula (II) is preferably 1.0 or more, and more preferably 1.1 or more, and it is preferably 2.0 or less, and more preferably 1.5 or less.

[18] The method for producing a 1,3-dioxan-5-one as set forth in any of [11] to [17], wherein the base is preferably a heterocyclic aromatic amine having a pyridine skeleton.

[19] The method for producing a 1,3-dioxan-5-one as set forth in [18], wherein the heterocyclic aromatic amine having a pyridine skeleton is preferably at least one selected from pyridine, 3,5-lutidine, 2,6-lutidine, 3-ethylpyridine, 4-ethylpyridine, and 5-ethyl-2-methylpyridine, and more preferably at least one selected from pyridine, 3,5-lutidine, 3-ethylpyridine, 4-ethylpyridine, and 5-ethyl-2-methylpyridine.

[20] The method for producing a 1,3-dioxan-5-one as set forth in any of [11] to [19], wherein a molar ratio of the base relative to the mixture of the compound represented by the formula (I) and the compound represented by the formula (II) is preferably 1.0 or more, more preferably 1.1 or more, still more preferably 1.2 or more, and yet still more preferably 1.3 or more, and it is preferably 2.5 or less, more preferably 2.0 or less, and still more preferably 1.7 or less.

[21] The method for producing a 1,3-dioxan-5-one as set forth in any of [1] to [20], wherein in the step 2, a solvent is preferably used, and the solvent is preferably a solvent selected from acetone, 2-butanone, cyclopentanone, acetonitrile, and dichloromethane; more preferably a solvent selected from acetone, 2-butanone, and acetonitrile; and still more preferably a solvent selected from acetone and 2-butanon.

[22] The method for producing a 1,3-dioxan-5-one as set forth in [21], wherein the use amount of the solvent relative to the whole of the reaction system is preferably 20% by mass or more, more preferably 30% by mass or more, still more preferably 40% by mass or more, yet still more preferably 50% by mass or more, and even yet still more preferably 60% by mass or more, and it is preferably 90% by mass or less, more preferably 85% by mass or less, and still more preferably 80% by mass or less.

[23] The method for producing a 1,3-dioxan-5-one as set forth in any of [1] to [22], wherein in the step 2, the oxidizing agent or oxidizing agent solution is preferably added to the mixture or the mixed solution containing the raw materials other than the oxidizing agent.

[24] The method for producing a 1,3-dioxan-5-one as set forth in [23], wherein a temperature of the reaction solution during dropping of the oxidizing agent or oxidizing agent solution is preferably −15° C. or higher, and more preferably −10° C. or higher, and it is preferably 25° C. or lower, and more preferably 10° C. or lower.

[25] The method for producing a 1,3-dioxan-5-one as set forth in [23] or [24], wherein after completion of dropping of the oxidizing agent or oxidizing agent solution, the reaction is continued until the dioxane and the dioxolane all react, or a lowering of the residual amount stops.

[26] The method for producing a 1,3-dioxan-5-one as set forth in [25], wherein the temperature of the reaction solution is preferably −10° C. or higher, and more preferably −5° C. or higher, and it is preferably 50° C. or lower, and more preferably 30° C. or lower.

[27] The method for producing a 1,3-dioxan-5-one as set forth in any of [1] to [26], wherein an alcohol is preferably used as a reaction terminator in the step 2.

[28] The method for producing a 1,3-dioxan-5-one as set forth in [27], wherein the reaction terminator is preferably a primary or secondary alcohol, and more preferably a secondary alcohol.

[29] The method for producing a 1,3-dioxan-5-one as set forth in [27] or [28], wherein the reaction terminator is preferably an alcohol having 1 or more and 12 or less carbon atoms.

[30] The method for producing a 1,3-dioxan-5-one as set forth in any of [1] to [29], wherein the step of oxidizing the mixture under an oxidative esterification condition (step 2) satisfies the following conditions 1 to 3.

Condition 1: The dioxanone is produced from the dioxane.
Condition 2: The ester dimer is produced from the dioxolane.
Condition 3: The yield of the formyl dioxolane produced from the dioxolane is 10% or less and 0% or more.

[31] The method for producing a 1,3-dioxan-5-one as set forth in any of [1] to [30], wherein the method includes, after the step 2, a step of separating the 1,3-dioxan-5-one (step 3).
[32] The method for producing a 1,3-dioxan-5-one as set forth in [31], wherein the separation in the step 3 is separation through distillation.
[33] The method for producing a 1,3-dioxan-5-one as set forth in [32], wherein the separation through distillation is preferably performed under rectification conditions.
[34] The method for producing a 1,3-dioxan-5-one as set forth in [33], wherein as for the rectification conditions, the number of theoretical stages of a rectifying tower is preferably 2 stages or more, and more preferably 5 stages or more, and a reflux ratio is preferably 0.1 or more, and more preferably 0.5 or more; and the number of theoretical stages of the rectifying tower is preferably 20 stages or less, and more preferably 10 stages or less, and the reflux ratio is preferably 20 or less, and more preferably 10 or less.
[35] A method for producing dihydroxyacetone, including subjecting the 1,3-dioxan-5-one separated in any of [31] to [34] to deacetalization.
[36] A method for producing 2-amino-1,3-propanediol, including subjecting the 1,3-dioxan-5-one separated in any of [31] to [34] to reductive amination, followed by deacetalization.
[37] A method for producing dihydroxyacetone, including a step of producing a 1,3-dioxan-5-one by the production method of any of [1] to [34]; and a step of subjecting the 1,3-dioxan-5-one produced by the foregoing step to deacetalization.
[38] A method for producing 2-amino-1,3-propanediol, including a step of producing a 1,3-dioxan-5-one by the production method of any of [1] to [34]; and a step of subjecting the 1,3-dioxan-5-one produced by the foregoing step to reductive amination, followed by deacetalization.
[39] A method for producing a 5-amino-1,3-dioxane, including a step of producing a 1,3-dioxan-5-one by the production method of any of [1] to [34]; and a step of subjecting the 1,3-dioxan-5-one produced by the foregoing step to reductive amination.

EXAMPLES

[Identification of Compound]
Each of compounds obtained in the following Production Examples, Examples, or Comparative Examples (hereinafter also referred to as "Examples and the like") was identified through spectral analysis with a nuclear magnetic resonance apparatus (NMR, manufactured by Agilent Technologies, model: Agilent 400-MR DD2), an infrared spectrophotometer (IR, manufactured by Horiba, Ltd., model: FT-710), and a gas chromatography mass spectrometer (GC-MS, manufactured by Agilent Technologies, model: Agilent 5975C).
[Purity Compound Produced or Purified]
The purity of each of compounds produced or purified in the following Examples and the like was determined through analysis (GC analysis) with a gas chromatograph (manufactured by Agilent Technologies, model: Agilent 6850). The term "%" regarding the purity means "GC %", and this value was used at the time of expressing in terms of a net quantity regarding the reaction raw materials and high-purity authentic samples.
[Unit, Conversion, and Yield]
The conversion of each of reaction raw materials and the yield of each of products shown in the following Examples and the like were determined through internal standard method quantitative GC analysis. A calibration curve necessary for the quantitative analysis was prepared using a commercially available authentic sample, or a high-purity authentic sample purified from a reaction mixture through distillation or silica gel column chromatography. However, the yield of a formyl dioxolane was calculated by substituting a calibration curve of a corresponding dioxanone.
[Measurement Conditions of GC and GC-MS]
Column: Ultra ALLOY-1 (MS/HT) (Frontier Laboratories Ltd. a trademark, inner diameter: 0.25 mm, film thickness: 0.15 μm, length: 30 m)
Carrier gas: Helium, 1.0 mL/min
Injection conditions: 250° C., split ratio: 1/50
Detection conditions: FID system, 220° C.
Column temperature conditions: After holding at 40° C. for 5 minutes, the temperature is raised to 350° C. at 10° C./min.
Internal standard compound: n-Dodecane
Ionization mode: EI
Ion source temperature: 230° C.
Interface temperature: 350° C.

Production Example 1: Production of a Mixture of 2-phenyl-1,3-dioxan-5-ol and 4-hydroxymethyl-2-phenyl-1,3-dioxolane as a Raw Material The reaction which was performed in Production Example 1 is as follows.

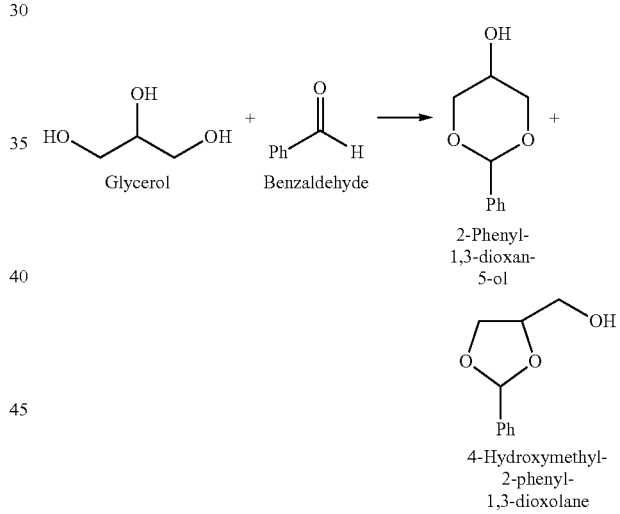

In a one-liter flask equipped with a Dean-Stark apparatus, 184 g of glycerol (purity: 100%, 2.00 mol), 238 g (purity: 98.0%, 2.20 mol) of benzaldehyde, 18 g of AMBERLYST 15DRY (strongly acidic cation exchange resin, manufactured by The Dow Chemical Company, a trademark), and 50 g of n-hexane were charged and refluxed for 6 hours while removing water by-produced by the reaction outside the reaction system. After cooling, the ion exchange resin was filtered off, and the filtrate was subjected to GC analysis. As a result, a reaction yield of an isomer mixture of four kinds composed of cis- and trans-2-phenyl-1,3-dioxan-5-ol and cis- and trans-4-hydroxymethyl-2-phenyl-1,3-dioxolane was 91%.

Subsequently, the filtrate was transferred into a 500-mL flask equipped with a Claisen head; after heating at 50° C., the pressure was gradually reduced to distill off the n-hexane; and simple distillation was further performed under reduced pressure of 0.13 kPa (absolute pressure), thereby obtaining 317 g of an isomer mixture which was distilled out as a colorless liquid at a fraction temperature of 110 to 120° C. The purity was 100%, and the distillation yield was 97%.

Reference Literature 5 (Journal of Catalysis, Vol. 245, pp. 428-435, 2007) describes $^1$H-NMR signal assignment of a proton at the 2-position of each isomer. An isomer ratio of 2-phenyl-1,3-dioxan-5-ol to 4-hydroxymethyl-2-phenyl-1,3-dioxolane determined from the information and the $^1$H-NMR analysis was 49/51.

<Spectral Data of Isomer Mixture>

IR (neat, cm$^{-1}$): 3429 (br), 2991, 2937, 2856, 1408, 1151, 1082, 1039

Production Example 2: Production of a Mixture of 2-phenyl-1,3-dioxan-5-ol and 4-hydroxymethyl-2-phenyl-1,3-dioxolane as a Raw Material The reaction which was performed in Production Example 2 is as follows.

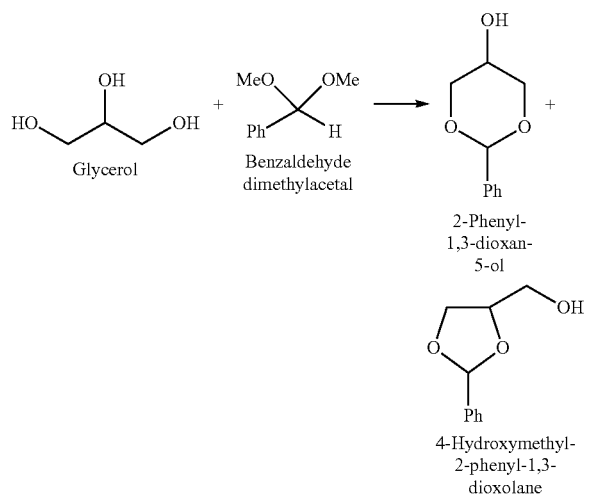

In a 100-mL flask, 9.21 g of glycerol (purity: 100%, 100 mmol), 17.1 g of benzaldehyde dimethylacetal (purity: 98.0%, 110 mmol), 0.50 g of AMBERLYST 36 (strongly acidic cation exchange resin, manufactured by The Dow Chemical Company, a trademark), and 23 g of dichloromethane were charged and stirred at 25° C. for 6 hours in a nitrogen atmosphere. The ion exchange resin was filtered off, and the dichloromethane was distilled off from the filtrate, followed by performing GC analysis. As a result, a reaction yield of an isomer mixture of four kinds composed of cis- and trans-2-phenyl-1,3-dioxan-5-ol and cis- and trans-4-hydroxymethyl-2-phenyl-1,3-dioxolane was 77%. In addition, an isomer ratio of 2-phenyl-1,3-dioxan-5-ol to 4-hydroxymethyl-2-phenyl-1,3-dioxolane determined from the information of Reference Literature 5 and the $^1$H-NMR analysis was 55/45.

Production Example 3: Production of a Mixture of 2-methyl-1,3-dioxan-5-ol and 4-hydroxymethyl-2-methyl-1,3-dioxolane as a Raw Material The reaction which was performed in Production Example 3 is as follows.

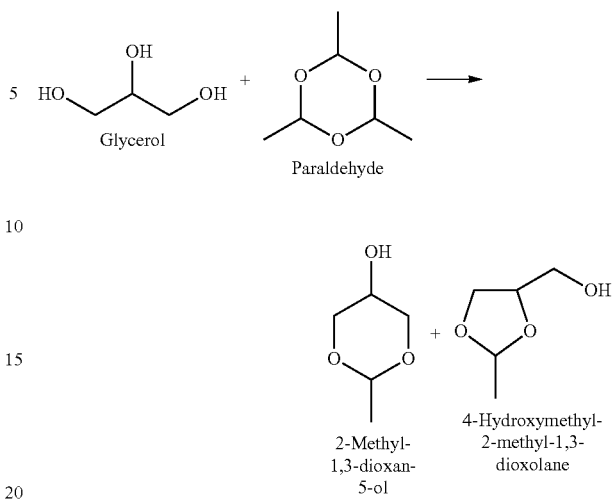

In a 500-mL flask equipped with a Dean-Stark apparatus, 184 g of glycerol (purity: 100%, 2.00 mol), 117 g of paraldehyde (purity: 98.0%, 868 mmol), 981 mg of methanesulfonic acid (purity: 98.0%, 10.0 mmol), and 40 g of n-hexane were charged and refluxed for 5 hours while removing water by-produced by the reaction outside the reaction system. After cooling, the reaction solution was neutralized with 3.50 g of a 20% ethanol solution of sodium ethoxide (700 mg as sodium ethoxide, 10.3 mmol). As a result of analyzing the reaction solution, a reaction yield of an isomer mixture of four kinds composed of cis- and trans-2-methyl-1,3-dioxan-5-ol and cis- and trans-4-hydroxymethyl-2-methyl-1,3-dioxolane was 71%.

Subsequently, the reaction solution was transferred into a 500-mL flask equipped with a Claisen head; after heating at 50° C., the pressure was gradually reduced to distill off the n-hexane and the ethanol; and simple distillation was further performed under reduced pressure of 0.67 kPa (absolute pressure), thereby obtaining 160 g of an isomer mixture composed of four kinds of cis- and trans-2-methyl-1,3-dioxan-5-ol and cis- and trans-4-hydroxymethyl-2-methyl-1,3-dioxolane, which was distilled out as a colorless liquid at a fraction temperature of 62 to 70° C. The purity was 100%, and the distillation yield was 96%.

Reference Literature 6 (Tetrahedron, Vol. 71, No. 20, pp. 3032-3038, 2015) describes $^1$H-NMR signal assignment of a proton at the 2-position of each isomer. An isomer ratio of 2-methyl-1,3-dioxan-5-ol to 4-hydroxymethyl-2-methyl-1,3-dioxolane determined from the information and the $^1$H-NMR analysis was 70/30.

<Spectral Data of Isomer Mixture>

IR (neat, cm$^{-1}$): 3415 (br), 2856, 1456, 1394, 1149, 1086

Production Example 4: Production of a Mixture of 2-n-heptyl-1,3-dioxan-5-ol and 4-hydroxymethyl-2-n-heptyl-1,3-dioxolane as a Raw Material The reaction which was performed in Production Example 4 is as follows.

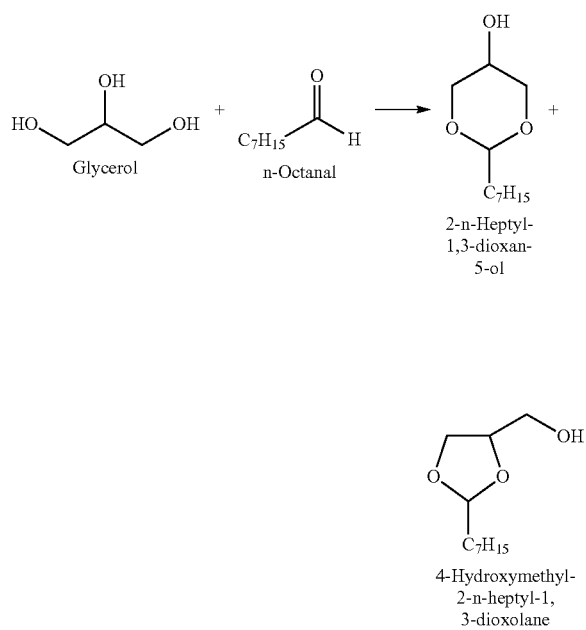

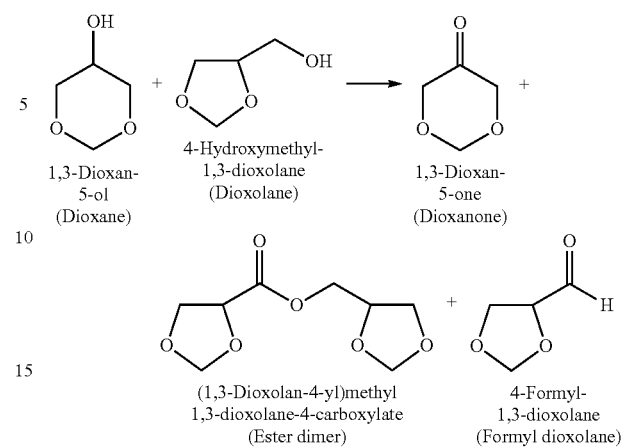

Example 1-1

In a 300-mL flask equipped with a Dean-Stark apparatus, 69.1 g of glycerol (purity: 100%, 750 mmol), 98.1 g of n-octanal (purity: 98.0%, 750 mmol), 368 mg of methanesulfonic acid (purity: 98.0%, 3.75 mmol), and 18 g of n-hexane were charged and refluxed for 3 hours while removing water by-produced by the reaction outside the reaction system. After cooling, the reaction solution was neutralized with 1.30 g of a 20% ethanol solution of sodium ethoxide (260 mg as sodium ethoxide, 3.82 mmol). As a result of analyzing the reaction solution, a reaction yield of an isomer mixture of four kinds composed of cis- and trans-2-n-heptyl-1,3-dioxan-5-ol and cis- and trans-4-hydroxymethyl-2-n-heptyl-1,3-dioxolane was 100%.

Subsequently, the reaction solution was transferred into a 200-mL flask equipped with a Claisen head; after heating at 50° C., the pressure was gradually reduced to distill off the n-hexane and the ethanol; and simple distillation was further performed under reduced pressure of 67 kPa (absolute pressure), thereby obtaining 135 g of an isomer mixture composed of four kinds of cis- and trans-2-n-heptyl-1,3-dioxan-5-ol and cis- and trans-4-hydroxymethyl-2-n-heptyl-1,3-dioxolane, which was distilled out as a colorless liquid at a fraction temperature of 95 to 102° C. The purity was 99%, and the distillation yield was 89%.

Reference Literature 7 (Green Chemistry, Vol. 12, pp. 2225-2231, 2010) describes $^1$H-NMR signal assignment of a proton at the 2-position of each isomer. An isomer ratio of 2-heptyl-1,3-dioxan-5-ol to 4-hydroxymethyl-2-heptyl-1,3-dioxolane determined from the information and the $^1$H-NMR analysis was 57/43.

<Spectral Data of Isomer Mixture>

IR (neat, cm$^{-1}$): 3479 (br), 2954, 2854, 1462, 1394, 1146, 1043

Example 1: Production of 1,3-Dioxan-5-one

The reaction which was performed in Example 1 is as follows.

In a one-liter flask equipped with a 100-mL dropping funnel, 63.7 g of a mixture of 1,3-dioxan-5-ol and 4-hydroxymethyl-1,3-dioxolane (a trade name: Glycerol Formal, manufactured by Tokyo Chemical Industry Co., Ltd., purity: 98.0%, 600 mmol, an isomer ratio of 1,3-dioxan-5-ol to 4-hydroxymethyl-1,3-dioxolane determined from the information of Reference Literature 5 and the $^1$H-NMR analysis: 58/42), 93.8 mg of 2-hydroxy-2-azaadamantane (AZADOL, a trademark, manufactured by Nissan Chemical Corporation, purity: 98.0%, 0.60 mmol), 71.5 g of pyridine (purity: 99.5%, 900 mmol), and 150 g of acetonitrile were charged and stirred in a nitrogen atmosphere while cooling. A solution of 58.7 g of trichloroisocyanuric acid (TCCA, purity: 95.0%, 240 mmol) dissolved in 150 g of acetonitrile was charged three separate times in the dropping funnel and dropped over 3.5 hours while regulating a dropping rate such that the reaction solution temperature within the flask fell within a range of from −2° C. to 2° C. The cooling was stopped, and the stirring was further continued for 4 hours while raising the reaction solution temperature to around 20° C. Finally, 7.23 g (purity: 99.7%, 120 mmol) of 2-propanol was added, and the stirring was further performed for 20 minutes, thereby completing the reaction. After filtering off a by-produced powdered solid, 100 g of tert-butyl methyl ether was added to the reaction solution from which the acetonitrile had been distilled off, and the filtration-off of the deposited powdered solution and the distillation-off of the solvent were repeated two times, thereby obtaining 70.5 g of an orange-colored oily crude product. As a result of GC analysis of the crude product, the conversion of 1,3-dioxan-5-ol was 100%; the yield of 1,3-dioxan-5-one was 90%; the conversion of 4-hydroxymethyl-1,3-dioxolane was 100%; the yield of (1,3-dioxolan-4-yl)methyl 1,3-dioxolane-4-carboxylate was 95%; and the yield of 4-formyl-1,3-dioxolane was 1%.

In a 200-mL pear shaped flask equipped with a packed distillation tower having the number of theoretical stages of 6 (packing: Helipack packing No. 2), 65.0 g of the crude product was charged, the pressure was reduced to 0.67 kPa (absolute pressure) while distilling off the residual solvent and pyridine, and a reflux ratio was then set to 3, thereby obtaining 27.4 g of a 1,3-dioxan-5-one which was distilled out as a colorless liquid at a fraction temperature of 42 to 43° C. The purity was 99.2%, and the distillation yield was 92%. Furthermore, the pressure was changed to 0.13 kPa (absolute pressure), and the reflux ratio was changed to 0.1, thereby obtaining 21.9 g of (1,3-dioxolan-4-yl)methyl 1,3-dioxolane-4-caboxylate which was distilled out as a pale yellow liquid at a fraction temperature of 89 to 91° C. The purity was 98.8%, and the distillation yield was 96%. $^{13}$C-NMR analysis suggested that the ester dimer was a stereoisomer mixture of four kinds composed of two pairs of racemates.

FIG. 1 is a GC chart of the reaction solution obtained in Example 1-1.

<Spectral Data of 1,3-Dioxan-5-one>

$^1$H-NMR (400 MHz, CDCl$_3$, $\delta_{ppm}$); 4.36 (4H, s), 5.02 (2H, s)

$^{13}$C-NMR (100 MHz, CDCl$_3$, $\delta_{ppm}$): 73.4, 91.4, 203.7

IR (neat, cm$^{-1}$): 2864, 1736, 1425, 1240, 1178, 1122, 1043, 930

MS (m/z): 102 (M$^+$), 73, 44

<Spectral Data of (1,3-Dioxolan-4-yl)methyl 1,3-dioxolane-4-caboxylate (Stereoisomer Mixture)>

IR (neat, cm$^{-1}$): 2956, 2856, 1751, 1284, 1151, 1082, 1016, 916

MS (m/z): 204 (M$^+$), 159, 129, 86, 73, 57, 45

<Spectral Data of 4-Formyl-1,3-dioxolane>

MS (m/z): 102 (M$^+$), 73, 56, 45

Example 1-2

In a 50-mL flask equipped with a 20-mL dropping funnel, 3.19 g of the same Glycerol Formal as in Example 1-1 (purity: 98.0%, 30.0 mmol), 4.7 mg of AZADOL (purity: 98.0%, 30 μmol), 4.77 g of pyridine (purity: 99.5%, 60.0 mmol), and 10 g of acetonitrile were charged and stirred in a nitrogen atmosphere while cooling. A solution of 2.94 g of TCCA (purity: 95.0%, 12.0 mmol) dissolved in 10 g of acetonitrile was charged in the dropping funnel and dropped over 1 hour while regulating a dropping rate such that the reaction solution temperature within the flask fell within a range of from −10° C. to 10° C. The cooling was stopped, and the stirring was further continued for 2 hours while raising the reaction solution temperature to around 25° C. Finally, 0.20 g (purity: 99.7%, 3.3 mmol) of 2-propanol was added, and the stirring was further performed for 10 minutes, thereby completing the reaction. After filtering off a by-produced powdered solid, the filtrate was subjected to GC analysis. As a result, the conversion of 1,3-dioxan-5-ol was 100%; the yield of 1,3-dioxan-5-one was 98%; the conversion of 4-hydroxymethyl-1,3-dioxolane was 100%; the yield of (1,3-dioxolan-4-yl)methyl 1,3-dioxolane-4-caboxylate was 99%; and the yield of 4-formyl-1,3-dioxolane was 1%.

Examples 1-3 to 1-15

The same operations as in Example 1-2 were followed, except for changing the kind or use amount of the catalyst, the kind or use amount of the base, or the solvent species. The reaction conditions and results of Examples 1-2 to 1-15 are shown in Table 1.

TABLE 1

| Example | Catalyst | | Oxidizing agent | | Base | | Solvent | Reaction time (hr)[2] | Conversion (%) | | Yield (%) | | |
|---|---|---|---|---|---|---|---|---|---|---|---|---|---|
| | Name | Molar ratio[1] | Name | Molar ratio[1] | Name | Molar ratio[1] | | | Dioxane | Dioxolane | Dioxanone | Ester dimer | Formyl dioxolane |
| 1-2 | AZADOL | 0.001 | TCCA | 0.40 | Pyridine | 2.0 | Acetonitrile | 3 | 100 | 100 | 98 | 99 | 1 |
| 1-3 | AZADOL | 0.001 | TCCA | 0.40 | Pyridine | 1.1 | Acetonitrile | 4 | 88 | 100 | 86 | 100 | 0 |
| 1-4 | AZADOL | 0.001 | TCCA | 0.40 | 3,5-Lutidine | 1.5 | Acetonitrile | 2 | 100 | 100 | 100 | 94 | 1 |
| 1-5 | AZADOL | 0.001 | TCCA | 0.40 | 2.6-Lutidine | 1.5 | Acetonitrile | 7 | 86 | Not analyzed | 81 | 78 | 9 |
| 1-6 | AZADOL | 0.001 | TCCA | 0.40 | 3-Ethylpyridine | 1.5 | Acetonitrile | 3 | 97 | 100 | 93 | 93 | 0 |
| 1-7 | AZADOL | 0.010 | TCCA | 0.40 | 5-Ethyl-2-methylpyridine | 1.5 | Acetonitrile | 2 | 100 | 100 | 100 | 66 | 0 |
| 1-8 | AZADOL | 0.002 | TCCA | 0.40 | 3,5-Lutidine | 1.5 | Acetone | 2 | 100 | 100 | 97 | 83 | 0 |
| 1-9 | AZADOL | 0.001 | TCCA | 0.40 | 3,5-Lutidine | 1.5 | 2-Butanone | 2 | 100 | 100 | 100 | 91 | 0 |
| 1-10 | AZADOL | 0.001 | TCCA | 0.40 | Pyridine | 1.5 | Cyclopentanone | 2 | 87 | 100 | 83 | 97 | Not analyzed |
| 1-11 | TEMPO | 0.010 | TCCA | 0.40 | 3,5-Lutidine | 1.5 | Acetonitrile | 6 | 94 | 100 | 79 | 100 | 0 |
| 1-12 | 4-OMe-TEMPO | 0.010 | TCCA | 0.40 | 3,5-Lutidine | 1.5 | Acetonitrile | 3 | 100 | 100 | 92 | 100 | 0 |
| 1-13 | 4-OBz-TEMPO | 0.010 | TCCA | 0.40 | 3,5-Lutidine | 1.5 | Acetonitrile | 3 | 100 | 100 | 94 | 91 | 2 |
| 1-14 | 4-NHAc-TEMPO | 0.001 | TCCA | 0.40 | 3,5-Lutidine | 1.5 | Acetone | 4 | 100 | 100 | 99 | 73 | 4 |
| 1-15 | 4-OMs-TEMPO | 0.005 | TCCA | 0.40 | Pyridine | 1.5 | 2-Butanone | 6 | 98 | 100 | 91 | 93 | 0 |

[1] Molar ratio to the mixture of 1,3-dioxan-5-ol and 4-hydroxymethyl-1,3-dioxolane

[2] Time from start of dropping to completion of reaction

Example 2: Production of 2-Phenyl-1,3-dioxan-5-one

The reaction which was performed in Example 2 is as follows.

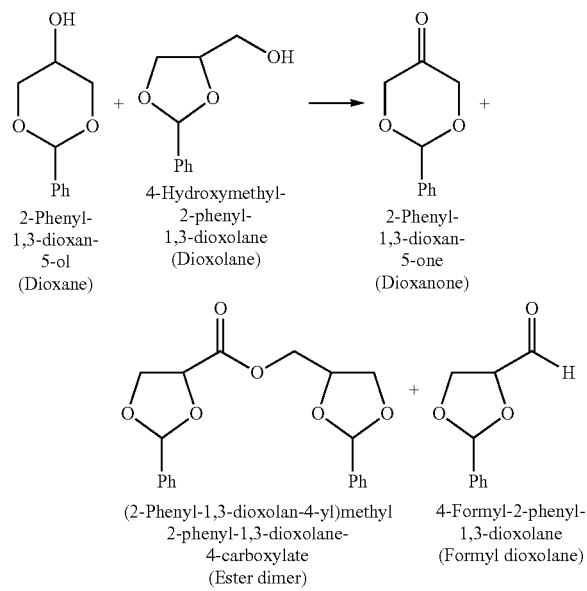

Examples 2-1 and 2-2

Using, as a reaction raw material, 3.60 g (purity: 100%, 20.0 mmol) of the mixture of 2-phenyl-1,3-dioxan-5-ol and 4-hydroxymethyl-2-phenyl-1,3-dioxolane obtained in Production Example 1, the same operations as in Example 1-2 were followed, thereby obtaining a reaction solution containing, as main products, of 2-phenyl-1,3-dioxan-5-one and (2-phenyl-1,3-dioxolan-4-yl)methyl 2-phenyl-1,3-dioxo-lane-4-caboxylate. The reaction conditions and results of Examples 2-1 and 2-2 are shown in Table 2.

The reaction solutions obtained in Examples 2-1 and 2-2 were mixed and subjected to simple distillation under reduced pressure of 0.13 kPa (absolute pressure). A pale yellow liquid which was distilled out at a fraction temperature of 94 to 96° C. was recrystallized from tert-butyl methyl ether, thereby obtaining 1.28 g of a colorless thin plate-like crystal of 2-phenyl-1,3-dioxan-5-one. The purity was 100%, and the purification yield was 43%. Furthermore, a component having an Rf value of 0.24 was separated by silica gel column chromatography of a dark brown oily simple distillation residue (developing solvent: n-hexane/ethyl acetate=3), and after solvent distillation-off and vacuum drying, 2.58 g of orange-colored liquid-like (2-phenyl-1,3-dioxolan-4-yl)methyl 2-phenyl-1,3-dioxolane-4-caboxylate was obtained. The purity was 90.6%, and the purification yield was 78%. According to the GC-MS analysis, the ester dimer was confirmed to be a stereoisomer mixture composed of at least six pairs of racemates. With respect to other two pairs of racemates, it is estimated that the peaks were overlapped, so that the detection could not be performed.

FIG. 2 is a GC chart of the reaction solution obtained in Example 2-1.

<Spectral Data of 2-Phenyl-1,3-dioxan-5-one>

$^1$H-NMR (400 MHz, CDCl$_3$, $\delta_{ppm}$): 4.46 (2H, d, J=17.2 Hz), 4.52 (2H, d, J=17.2 Hz), 5.89 (1H, s), 7.25-7.55 (5H, m)

$^{13}$C-NMR (100 MHz, CDCl$_3$, $\delta_{ppm}$): 72.4, 99.0, 126.1, 128.5, 129.4, 133.8, 204.4

IR (neat, cm$^{-1}$): 3070, 2860, 1718, 1394, 1094, 975

MS (m/z): 178 (M$^+$), 148, 119, 105, 91, 77, 51

<Spectral Data of (2-Phenyl-1,3-dioxolan-4-yl)methyl 2-phenyl-1,3-dioxolane-4-caboxylate (Stereoisomer Mixture)>

IR (neat, cm$^{-1}$): 2881, 1751, 1734, 1458, 1394, 1200, 1080, 648

MS (m/z, common to six peaks on GC): 356 (M$^+$), 250, 233, 149, 129, 105, 91, 77, 55

<Spectral Data of 4-Formyl-2-phenyl-1,3-dioxolane (Stereoisomer Mixture)>

MS (m/z, common to two peaks on GC): 178 (M$^+$), 177, 149, 105, 91, 77, 51

Example 2-3

In a 50-mL flask equipped with a dropping funnel, 451 mg (purity: 100%, 2.50 mmol) of the mixture of 2-phenyl-1,3-dioxan-5-ol and 4-hydroxymethyl-2-phenyl-1,3-dioxolane obtained in Production Example 1, 1.98 g (purity: 95.0%, 6.26 mmol) of 4-acetamido-2,2,6,6-tetramethyl-1-oxopiperidinum tetrafluoroborate, 1.0 g of molecular sieve 4A which had been previously dried under vacuum heating conditions, and 10 g of dichloromethane were charged and stirred at room temperature in a nitrogen atmosphere. A solution composed of 0.457 g (purity: 99.5%, 5.75 mmol) of pyridine and 5 g of dichloromethane was charged in a 20-mL dropping funnel and dropped over 10 minutes. Furthermore, after further continuing the stirring at room temperature for 2 hours, 0.10 g (purity: 99.8%, 3.1 mmol) of methanol was finally added, and the stirring was further performed for 10 minutes, thereby completing the reaction. After separating the molecular sieve 4A and a by-produced powdered solid from each other through filtration, the filtrate was subjected to GC analysis. As a result, the conversion of 2-phenyl-1,3-dioxan-5-ol was 56%; the yield of 2-phenyl-1,3-dioxan-5-one was 13%; the conversion of 4-hydroxymethyl-2-phenyl-1,3-dioxolane was 60%; the yield of (2-phenyl-1,3-dioxolan-4-yl)methyl 2-phenyl-1,3-dioxolane-4-carboxylate was 51%; and the yield of 4-formyl-2-phenyl-1,3-dioxolane was 4%.

TABLE 2

| Example | Catalyst Name | Molar ratio [1] | Oxidizing agent Name | Molar ratio [1] | Base Name | Molar ratio [1] | Solvent | Reaction time (hr) [2] | Conversion (%) Dioxane | Conversion (%) Dioxolane | Yield (%) Dioxanone | Yield (%) Ester dimer | Yield (%) Formyl dioxolane |
|---|---|---|---|---|---|---|---|---|---|---|---|---|---|
| 2-1 | AZADOL | 0.010 | TCCA | 0.40 | Pyridine | 2.0 | Acetonitrile | 2 | 100 | 100 | 100 | 99 | 0.5 |
| 2-2 | AZADOL | 0.010 | $^t$BuOCl | 2.0 | Pyridine | 2.0 | Acetonitrile | 2 | 100 | 100 | 70 | 82 | 0.4 |

TABLE 2-continued

| | Catalyst | | Oxidizing agent | | Base | | | Reaction | Conversion (%) | Yield (%) | | | |
|---|---|---|---|---|---|---|---|---|---|---|---|---|---|
| Example | Name | Molar ratio [1] | Name | Molar ratio [1] | Name | Molar ratio [1] | Solvent | time (hr) [2] | Diox-ane | Diox-olane | Diox-anone | Ester dimer | Formyl dioxolane |
| 2-3 | 4-NHAc-TEMPO salt [3] | 2.50 | — | | — | | Pyridine | 2.3 | Dichloromethane | 2 | 56 | 60 | 13 | 51 | 4 |

[1] Molar ratio to the mixture of 2-phenyl-1,3-dioxan-5-ol and 4-hydroxymethyl-2-phenyl-1,3-dioxolane
[2] Time from start of dropping to completion of reaction
[3] 4-Acetamido-2,2,6,6-tetramethyl-1-oxopiperidinum tetrafluoroborate Example 3: Production of 2-Methyl-1,3-dioxan-5-one The reaction which was performed in Example 3 is as follows.

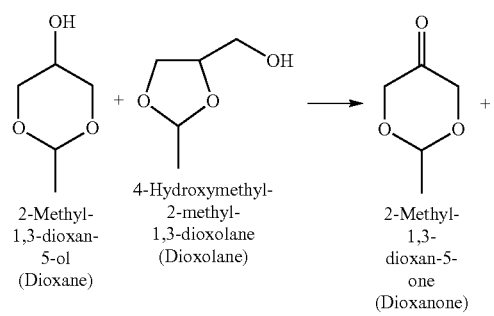

2-Methyl-1,3-dioxan-5-ol (Dioxane)

4-Hydroxymethyl-2-methyl-1,3-dioxolane (Dioxolane)

2-Methyl-1,3-dioxan-5-one (Dioxanone)

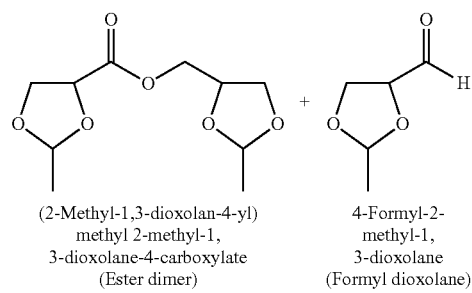

(2-Methyl-1,3-dioxolan-4-yl)methyl 2-methyl-1,3-dioxolane-4-carboxylate (Ester dimer)

4-Formyl-2-methyl-1,3-dioxolane (Formyl dioxolane)

Example 3-1

Using, as a reaction raw material, 70.9 g (purity: 100%, 600 mmol) of the mixture of 2-methyl-1,3-dioxan-5-ol and 4-hydroxymethyl-2-methyl-1,3-dioxolane obtained in Production Example 3, the same operations as in Example 1-1 were followed, thereby obtaining 66.2 g of a yellow oily crude product. As a result of GC analysis of the crude product, the conversion of 2-methyl-1,3-dioxan-5-ol was 100%; the yield of 2-methyl-1,3-dioxan-5-one was 74%; the conversion of 2-methyl-4-hydroxymethyl-1,3-dioxolane was 100%; the yield of (2-methyl-1,3-dioxolan-4-yl)methyl 2-methyl-1,3-dioxolane-4-caboxylate was 88%; and the yield of 4-formyl-1,3-dioxolane was 0%.

In a 100-mL pear shaped flask equipped with a packed distillation tower having the number of theoretical stages of 6 (packing: Helipack packing No. 2), 60.0 g of the crude product was charged, the pressure was reduced to 1.3 kPa (absolute pressure) while distilling off the residual solvent and pyridine, and a reflux ratio was then set to 3, thereby obtaining 31.4 g of 2-methyl-1,3-dioxan-5-one which was distilled out as a colorless liquid at a fraction temperature of 52 to 53° C. The purity was 100%, and the distillation yield was 96%. Furthermore, the pressure was reduced to 0.13 kPa (absolute pressure), and the reflux ratio was then set to 0.5, thereby obtaining 16.1 g of (2-methyl-1,3-dioxolan-4-yl)methyl 2-methyl-1,3-dioxolane-4-caboxylate which was distilled out as a pale yellow liquid at a fraction temperature of 110 to 113° C. The purity was 98.6%, and the distillation yield was 95%. According to $^{13}$C-NMR and GC-MS analyses, the ester dimer was confirmed to be a stereoisomer mixture of four kinds composed of at least two pairs of racemates. With respect to other six pairs of racemates, it is estimated that the peaks were overlapped, so that the detection could not be performed.

<Spectral Data of 2-Methyl-1,3-dioxan-5-one>

$^1$H-NMR (400 MHz, CDCl$_3$, δ$_{ppm}$): 1.44 (3H, d, J=5.2 Hz), 4.29 (2H, d, J=17.6 Hz), 4.39 (2H, d, J=17.6 Hz), 5.06 (1H, q, J=5.2 Hz)

$^{13}$C-NMR (100 MHz, CDCl$_3$, δ$_{ppm}$): 20.2, 72.6, 97.4, 204.4

IR (neat, cm$^{-1}$): 2994, 2875, 1739, 1408, 1130, 1097, 1051, 872

MS (m/z): 116 (M$^+$), 101, 86, 58, 43

<Spectral Data of (2-Methyl-1,3-dioxolan-4-yl)methyl 2-methyl-1,3-dioxolane-4-caboxylate (Stereoisomer Mixture)>

IR (neat, cm$^{-1}$): 2991, 2864, 1751, 1408, 1201, 1146, 1088, 1076, 858

MS (m/z, common to two peaks on GC): 232 (M$^+$), 217, 173, 129, 101, 87, 59, 43

Examples 3-2 to 3-4

Using, as a reaction raw material, 3.54 g (purity: 100%, 30.0 mmol) of the mixture of 2-methyl-1,3-dioxan-5-ol and 4-hydroxymethyl-2-methyl-1,3-dioxolane obtained in Production Example 3, the same operations as in Example 1-2 were followed, thereby obtaining a reaction solution containing, as main products, 2-methyl-1,3-dioxan-5-one and (2-methyl-1,3-dioxolan-4-yl)methyl 2-methyl-1,3-dioxolane-4-caboxylate. The reaction conditions and results of Examples 3-2 to 3-4 are shown in Table 3.

TABLE 3

| Example | Catalyst Name | Molar ratio [1] | Oxidizing agent Name | Molar ratio [1] | Base Name | Molar ratio [1] | Solvent | Reaction time (hr) [2] | Conversion (%) Dioxane | Dioxolane | Yield (%) Dioxanone | Ester dimer | Formyl dioxolane |
|---|---|---|---|---|---|---|---|---|---|---|---|---|---|
| 3-2 | 4-NHAc-TEMPO | 0.010 | TCCA | 0.40 | 3.5-Lutidine | 1.5 | Acetonitrile | 2 | 100 | 100 | 90 | 94 | 0 |
| 3-3 | AZADOL | 0.010 | TCCA | 0.40 | 3.5-Lutidine | 1.3 | Acetonitrile | 2 | 100 | 100 | 78 | 99 | 1 |
| 3-4 | 4-OBz-TEMPO | 0.010 | TCCA | 0.40 | 3.5-Lutidine | 1.3 | Acetonitrile | 2 | 100 | 100 | 71 | 95 | 0 |

[1] Molar ratio to the mixture of 2-methyl-1,3-dioxan-5-ol and 4-hydroxymethyl-2-methyl-1,3-dioxolane
[2] Time from start of dropping to completion of reaction <Spectral Data of 2-Methyl-4-formyl-1,3-dioxolane (Stereoisomer Mixture)>

MS (m/z, common to two peaks on GC): 115, 101, 87, 71, 59, 43

FIG. 3 is a GC chart of the reaction solution obtained in Example 3-3.

Example 4: Production of 2-n-heptyl-1,3-dioxan-5-one

The reaction which was performed in Example 4 is as follows.

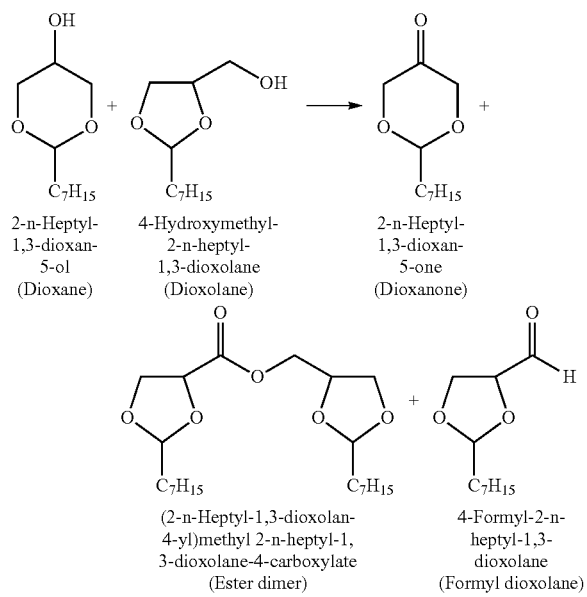

2-n-Heptyl-1,3-dioxan-5-ol (Dioxane)
4-Hydroxymethyl-2-n-heptyl-1,3-dioxolane (Dioxolane)
2-n-Heptyl-1,3-dioxan-5-one (Dioxanone)
(2-n-Heptyl-1,3-dioxolan-4-yl)methyl 2-n-heptyl-1,3-dioxolane-4-carboxylate (Ester dimer)
4-Formyl-2-n-heptyl-1,3-dioxolane (Formyl dioxolane)

Using, as a reaction raw material, 4.34 g (purity: 99.2%, 21.3 mmol) of the mixture of 2-n-heptyl-1,3-dioxan-5-ol and 4-hydroxymethyl-2-n-heptyl-1,3-dioxolane obtained in Production Example 4, the same reaction operations as in Example 1-1 were followed. For the purposes of filtration of a powdered solid and removal of a powdered solid redeposited after distilling off acetonitrile, 20 g of tert-butyl methyl ether and 10 g of ion exchanged water were added, and a saturated sodium hydrogencarbonate aqueous solution was further added until the pH of the aqueous layer became 8, followed by extraction. After static layer separation, the lower layer water was drawn out, 20 g of a saturated sodium chloride aqueous solution was added, and an operation of from extraction to drawing-out of the lower layer water was repeated. The resulting organic layer was dried over 10 g of anhydrous sodium sulfate, and after filtration, the tert-butyl methyl ether was distilled out, thereby obtaining 5.40 g of a pale yellow oily crude product. As a result of GC analysis of the crude product, the conversion of 2-n-heptyl-1,3-dioxan-5-ol was 93%; the yield of 2-n-heptyl-1,3-dioxan-5-one was 74%; the conversion of 2-n-heptyl-4-hydroxymethyl-1,3-dioxolane was 100%; the yield of (2-n-heptyl-1,3-dioxolan-4-yl)methyl 2-n-heptyl-1,3-dioxolane-4-caboxylate was 98%; and the yield of 4-formyl-n-heptyl-1,3-dioxolane was 2%.

Subsequently, 5.00 g of the crude product was distilled under reduced pressure of 40 Pa (absolute pressure) with a Kugelrohr distillation apparatus, thereby obtaining 1.35 g of 2-n-heptyl-1,3-dioxan-5-one which was distilled out as a colorless liquid at an apparatus temperature of 140 to 160° C. The purity was 97%, and the distillation yield was 78%. In addition, the purity of (2-n-heptyl-1,3-dioxolan-4-yl)methyl 2-n-heptyl-1,3-dioxolane-4-carboxylate in 1.86 g of a yellow gel-like distillation residue was 87%, and the distillation yield was 95%. According to $^{13}$C-NMR and GC-MS analyses, the ester dimer was confirmed to be a stereoisomer mixture of 16 kinds composed of eight pairs of racemates.

<Spectral Data of 2-n-heptyl-1,3-dioxan-5-one>

$^1$H-NMR (400 MHz, CDCl$_3$, $\delta_{ppm}$); 0.88 (3H, t, J=6.8 Hz), 1.23-1.37 (8H, m), 1.40-1.47 (2H, m), 1.69-1.74 (2H, m), 4.28 (2H, d, J=18.2 Hz), 4.40 (2H, d, J=18.2 Hz), 4.86 (1H, t, J=5.0 Hz)

$^{13}$C-NMR (100 MHz, CDCl$_3$, $\delta_{ppm}$); 14.0, 22.6, 24.0, 29.1, 29.3, 31.7, 34.0, 72.2, 100.4, 204.5

IR (neat, cm$^{-1}$); 2956, 2858, 1741, 1134, 1053, 957

MS (m/z); 200 (M$^+$), 101, 71, 55, 43

<Spectral Data n-Heptyl-1,3-dioxolan-4-yl)methyl 2-n-heptyl-1,3-dioxolane-4-caboxylate (Stereoisomer Mixture)>

IR (neat, cm$^{-1}$); 2925, 2854, 1747, 1458, 1198, 1147, 949

MS (m/z, common to eight peaks on GC); 400 (M$^+$), 301, 173, 157, 101, 69, 57, 43

<Spectral Data of 4-Formyl-n-heptyl-1,3-dioxolane (Stereoisomer Mixture)>

MS (m/z, common to two peaks on GC); 200 (Mt), 171, 101, 69, 55, 41

FIG. 4 is a GC chart of the reaction solution obtained in Example 4.

Example 5: Production of Dihydroxyacetone

The reaction which was performed in Example 5 is as follows.

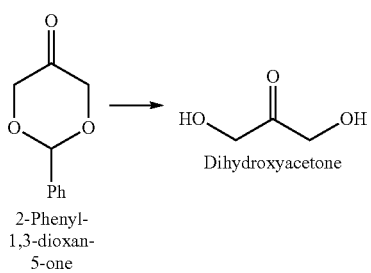 [SMILES: O=C1COC(c2ccccc2)OC1 ; O=C(CO)CO]

2-Phenyl-1,3-dioxan-5-one → Dihydroxyacetone

In a 20-mL flask, 1.00 g (purity: 100%, 5.61 mmol) of 2-phenyl-1,3-dioxan-5-one obtained in Examples 2-1 and 2-2, 1.0 g of DOWEX 50W×8 (strongly acidic cation exchange resin, manufactured by The Dow Chemical Company, a trademark), and 10 g of ion exchanged water were charged and stirred at 40° C. for 2 hours. After cooling, the reaction solution from which the ion exchange resin had been filtered off was extracted three times with 10 g of tert-butyl methyl ether, thereby removing the benzaldehyde. 100 g of acetonitrile was added to the aqueous solution, and the solvent was distilled off at 40° C., followed by vacuum drying. 500 mg of the resulting pale yellow resin-like crude product was subjected to trimethylsilylation (TMS), followed by GC analysis. As a result, the main products were DHA and a cyclic hemiacetal dimer of DHA. Reference Literature 8 (Journal of Catalysis, Vol. 245, pp. 428-435, 2007) describes ¹H-NMR signal assignment of DHA in heavy water. As a result of ¹H-NMR analysis of the crude product under the same conditions, DHA and a hydrate of DHA (molar ratio: 1.0/0.26) were main constituent substances similarly in the literature reference, and besides, a small amount of a hemiacetal dimer was existent. As a result of ¹H-NMR analysis of the crude product to which dimethyl sulfone had been added as an internal standard substance, the purity of the DHA skeleton in the crude product as determined through quantification of DHA and the hydrate of DHA was 63.3%, and the yield was 63%.

Example 6: Production of 2-Amino-1,3-propanediol (Serinol)

The reaction which was performed in Example 6 is as follows.

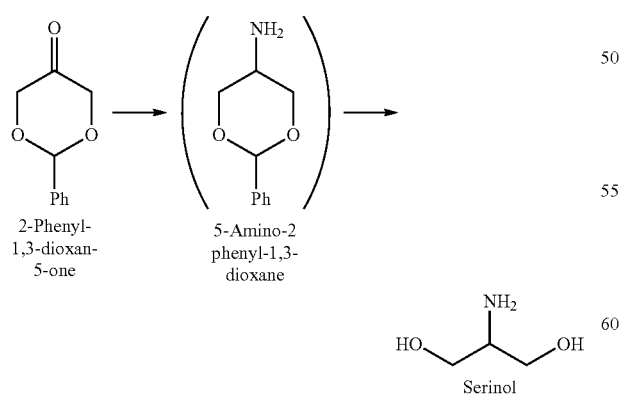

2-Phenyl-1,3-dioxan-5-one → 5-Amino-2-phenyl-1,3-dioxane → Serinol

In a 200-mL flask equipped with a 20-mL dropping funnel, 14.2 g (purity: 100%, 224 mmol) of ammonium formate, 0.50 g of 10%-palladium-on-carbon (manufactured by Kawaken Fine Chemicals Co., Ltd., MA type, 52% water-containing product), and 60 g of methanol were charged, and stirring was commenced. Immediately thereafter, a solution in which 4.00 g (purity: 100%, 22.4 mmol) of 2-phenyl-1,3-dioxan-5-one obtained in the same method as in Examples 2-1 and 2-2 was dissolved in 15 g of methanol was dropped from the dropping funnel over 30 minutes (during this, the temperature of the liquid in the flask raised from 17° C. to 20° C.), followed by further stirring for 2 hours. After filtering off the palladium-on-carbon and distilling off the methanol, a 2 mol/L sodium hydroxide solution was added until the pH reached 12, followed by extraction three times with 50 g of tert-butyl methyl ether. After distilling off the tert-butyl methyl ether from the gathered organic layer, 2.04 g of 5-amino-2-phenyl-1,3-dioxane which was distilled out as a colorless liquid under reduced pressure of 130 Pa (absolute pressure) with a Kugelrohr distillation apparatus at an apparatus temperature of 170 to 180° C. was obtained. To thus-obtained 5-amino-2-phenyl-1,3-dioxane, 40 mL of 2 mol/L hydrochloric acid was added and stirred at around 20° C. for 2 hours. The resultant was extracted three times with 50 mL of tert-butyl methyl ether to remove the benzaldehyde, and a 1 mol/L sodium hydroxide solution was then added until the pH reached 10. After distilling off the water, 10 mL of 2-propanol was added, an insoluble matter was separated through filtration, and the 2-propnal was further distilled off, followed by vacuum drying to obtain 1.10 g of a colorless oily crude product. As a result of ¹H-NMR analysis of the crude product to which dimethyl sulfone had been added as an internal standard substance in heavy water, the purity of serinol was 90.8%, and the yield was 49%.

INDUSTRIAL APPLICABILITY

In accordance with the production method of a 1,3-dioxan-5-one according to the present invention, a method of producing a 1,3-dioxan-5-one is provided by a short-step and simple method from raw materials that are procurable easily and inexpensively. The 1,3-dioxan-5-one obtained by the present invention is important as a synthetic intermediate for various useful compounds, is useful as a synthetic raw material of DHA or serinol, and is suitably used as raw materials for medicaments, chemical products, and the like.

The invention claimed is:

1. A method for producing a 1,3-dioxan-5-one, comprising using a mixture of a compound represented by the following formula (I) and a compound represented by the following formula (II) as a raw material, the method comprising a step of oxidizing the mixture under an oxidative esterification condition defined as obtaining one molecule of an ester dimer from two molecules of the same primary alcohol (step 2):

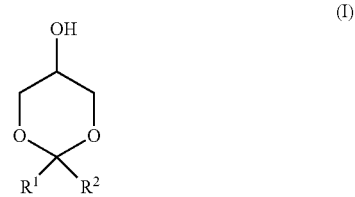

(I)

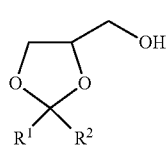
(II)

wherein, in the formulae (I) and (II), $R^1$ and $R^2$ each independently represent a hydrogen atom or a monovalent hydrocarbon group, or $R^1$ and $R^2$ are bonded to each other to form a divalent hydrocarbon group for constituting a ring structure.

2. The method for producing a 1,3-dioxan-5-one according to claim 1, wherein in the formulae (I) and (II), $R^1$ is a hydrogen atom.

3. The method for producing a 1,3-dioxan-5-one according to claim 1, wherein in the step 2, (a) at least one compound selected from an organic nitroxyl radical, an N-hydroxy form thereof, and a salt containing an oxo ammonium cation of an organic nitroxyl radical, (b) an oxidizing agent, and (c) a base are used.

4. The method for producing a 1,3-dioxan-5-one according to claim 3, wherein the organic nitroxyl radical is a compound represented by the following formula (VIII), a compound represented by the following formula (IX), or a compound represented by the following formula (X):

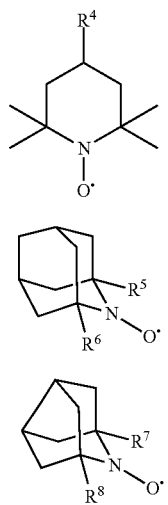

wherein, in the formula (VIII), $R^4$ represents a hydrogen atom, a halogen atom, a hydroxy group, an alkoxy group, an acyloxy group, an alkoxy carbonyl group, an amino group, an acylamino group, a sulfonyloxy group, an N-alkylcarbamoyloxy group, a carboxy group, a cyano group, an isocyanato group, an isothiocyanato group, or an oxo group; in the formula (IX), $R^5$ and $R^6$ each independently represent a hydrogen atom or a methyl group; and, in the formula (X), $R^7$ and $R^8$ each independently represent a hydrogen atom or a methyl group.

5. The method for producing a 1,3-dioxan-5-one according to claim 3, wherein the oxidizing agent is an oxidizing agent composed of a compound containing chlorine.

6. The method for producing a 1,3-dioxan-5-one according to claim 3, wherein the base is a heterocyclic aromatic amine having a pyridine skeleton.

7. The method for producing a 1,3-dioxan-5-one according to claim 1, comprising, after the step 2, a step of separating the 1,3-dioxan-5-one (step 3).

8. The method for producing a 1,3-dioxan-5-one according to claim 7, wherein the separation in the step 3 is separation through distillation.

9. The method for producing a 1,3-dioxan-5-one according to claim 1, wherein the mixture of a compound represented by the following formula (I) and a compound represented by the following formula (II) is produced by a method of acetalizing glycerol, and a compound represented by the following formula (V) or a multimer thereof in the presence of an acid catalyst (method 1), or a method of subjecting glycerol and a compound represented by the following formula (VI) to acetal exchange in the presence of an acid catalyst (method 2):

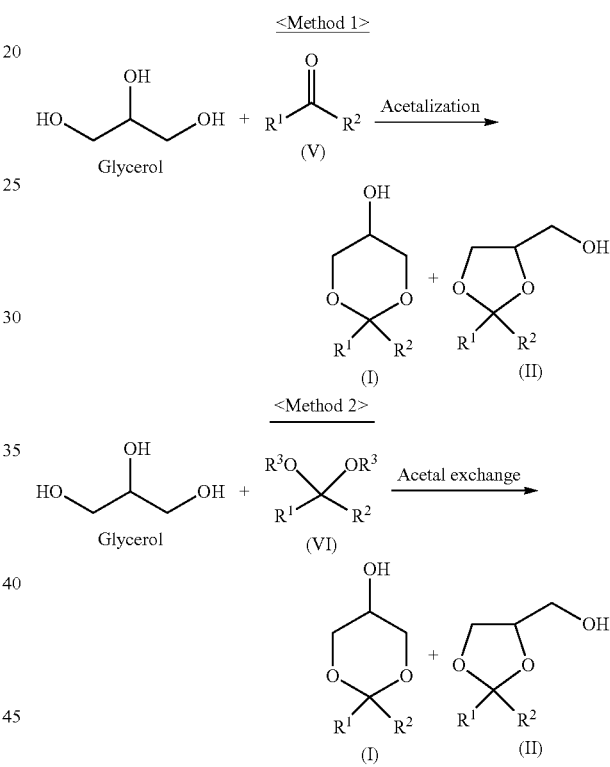

in the formulae (V) and (VI), $R^1$ and $R^2$ are synonymous with $R^1$ and $R^2$ in the formula (I) or (II), and in the formula (VI), $R^3$'s each independently represent a monovalent hydrocarbon group.

10. The method for producing a 1,3-dioxan-5-one according to claim 1, wherein in the step 2, an oxidation method selected from
an oxidation method of using a salt containing an oxo ammonium cation of an organic nitroxyl radical and a base; and
an oxidation method of using a compound selected from an organic nitroxyl radical, an N-hydroxy form thereof, and a salt containing an oxo ammonium cation of an organic nitroxyl radical, an oxidizing agent, and a base.

11. The method for producing a 1,3-dioxan-5-one according to claim 10, wherein an amount of the compound selected from the organic nitroxyl radical, the N-hydroxy form thereof, and the salt containing an oxo ammonium cation of an organic nitroxyl radical is 0.0001 or more and 0.1 or less in a molar ratio relative to the mixture of the compound represented by the formula (I) and the compound represented by the formula (II).

12. The method for producing a 1,3-dioxan-5-one according to claim 6, wherein the heterocyclic aromatic amine having a pyridine skeleton is at least one selected from pyridine, 3,5-lutidine, 2,6-lutidine, 3-ethylpyridine, 4-ethylpyridine, and 5-ethyl-2-methylpyridine.

13. The method for producing a 1,3-dioxan-5-one according to claim 1, wherein in the step 2, a solvent is used, which is selected from acetone, 2-butanone, cyclopentanone, acetonitrile, and dichloromethane.

14. The method for producing a 1,3-dioxan-5-one according to claim 1, wherein the step of oxidizing the mixture under an oxidative esterification condition (step 2) satisfies the following conditions 1 to 3;
- Condition 1: The dioxanone is produced from the dioxane,
- Condition 2: The ester dimer is produced from the dioxolane, and
- Condition 3: The yield of the formyl dioxolane produced from the dioxolane is 10% or less and 0% or more.

\* \* \* \* \*